(12) United States Patent
Poyet et al.

(10) Patent No.: US 10,358,469 B2
(45) Date of Patent: Jul. 23, 2019

(54) METHODS AND PHARMACEUTICAL COMPOSITIONS FOR THE TREATMENT OF CANCER

(71) Applicants: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR); ASSISTANCE PUBLIQUE-HÔPITAUX DE PARIS (APHP), Paris (FR)

(72) Inventors: Jean-Luc Poyet, Paris (FR); Heriberto Bruzzoni-Giovanelli, Paris (FR); Léonard Jagot-Lacoussiere, Paris (FR)

(73) Assignees: INSERM (INSTITUT NATIONAL DE LA SANTE ET DE LA RECHERCHE MEDICALE), Paris (FR); UNIVERSITE PARIS DIDEROT—PARIS 7, Paris (FR); ASSISTANCE PUBLIQUE—HOPITAUX DE PARIS (APHP), Paris (FR)

( * ) Notice: Subject to any disclaimer, the term of this patent is extended or adjusted under 35 U.S.C. 154(b) by 124 days.

(21) Appl. No.: 15/119,274

(22) PCT Filed: Feb. 17, 2015

(86) PCT No.: PCT/EP2015/053307
§ 371 (c)(1),
(2) Date: Aug. 16, 2016

(87) PCT Pub. No.: WO2015/121496
PCT Pub. Date: Aug. 20, 2015

(65) Prior Publication Data
US 2017/0058010 A1 Mar. 2, 2017

(30) Foreign Application Priority Data
Feb. 17, 2014 (EP) .................................... 14305210

(51) Int. Cl.
*C07K 14/47* (2006.01)
*C07K 14/005* (2006.01)
*C12N 7/00* (2006.01)
*A61K 38/00* (2006.01)

(52) U.S. Cl.
CPC ........ *C07K 14/4747* (2013.01); *C07K 14/005* (2013.01); *C07K 14/4703* (2013.01); *C12N 7/00* (2013.01); *A61K 38/00* (2013.01); *C07K 2319/10* (2013.01); *C07K 2319/73* (2013.01); *C12N 2740/16322* (2013.01)

(58) Field of Classification Search
CPC .......... C12N 2310/351; C12N 2320/31; A61K 38/00; G16B 20/00; G16B 25/00
See application file for complete search history.

(56) References Cited

U.S. PATENT DOCUMENTS

| | | | | |
|---|---|---|---|---|
| 5,608,035 | A * | 3/1997 | Yanofsky | ............. C07K 14/545 530/324 |
| 2003/0104622 | A1 * | 6/2003 | Robbins | ................... C07K 7/06 435/455 |

OTHER PUBLICATIONS

Van den Berghe et al. FIF [Fibroblast Growth Factor-2 (FGF-2)-Interacting-Factor], a Nuclear Putatively Antiapoptotic Factor, Interacts Specifically with FGF-2. Molecular Endocrinology, vol. 14, Issue 11, Nov. 1, 2000, pp. 1709-1724. (Year: 2000).*
Rooy et al. Identification of Peptide Ligands for Targeting to the Blood-Brain Barrier. Pharmaceutical Research, vol. 27, No. 4, Apr. 2010. (Year: 2010).*
Sommer et al. Proteolysis of peptide dendrimers. Chembiochem. Jun. 15, 2009;10(9):1527-36. (Year: 2009).*
Rigou et al., "The antiapoptotic protein AAC-11 interacts with and regulates Acinus-mediated DNA fragmentation", The EMBO Journal, Jun. 3, 2009, pp. 1576-1588, vol. 28, No. 11.
Snyder et al., "Treatment of Terminal Peritoneal Carcinomas by a Transducible p53-Activiating Peptide", Nature Reviews Cancer, Feb. 17, 2014, pp. 0186-0193, vol. 2, No. 2.
Audrey et al., "Targeting AAC-11 in cancer therapy", Expert Opinion on Therapeutic Targets, Jan. 2010, pp. 57-65, vol. 14, No. 1.
Tewari et al: "AAC-11, a Novel cDNA That INhibits Apoptosis after Growth Factor Withdrawal", American Association for Cancer Research, vol. 57, No. 18, pp. 4063-4069, Sep. 15, 1997.

* cited by examiner

*Primary Examiner* — Marcela M Cordero Garcia
*Assistant Examiner* — Jia-Hai Lee
(74) *Attorney, Agent, or Firm* — W&C IP

(57) ABSTRACT

The present invention relates to methods and pharmaceutical compositions for the treatment of cancer. In particular, the present invention relates to a polypeptide comprising or consisting of i) an amino acid sequence ranging from the phenylalanine residue at position 380 to the leucine residue at position 384 in SEQ ID NO: 1 or, ii) an amino acid sequence having at least 70% of identity with the amino acid sequence ranging from the phenylalanine residue at position 380 to the leucine residue at position 384 in SEQ ID NO: 1, or iii) an amino acid sequence which is a retro-inverso of the amino acid sequence ranging from the phenylalanine residue at position 380 to the leucine residue at position 384 in SEQ ID NO: 1 or, iv) an amino acid sequence which is retro-inverso of the amino acid sequence having at least 70% of identity with the amino acid sequence ranging from the phenylalanine residue at position 380 to the leucine residue at position 384 in SEQ ID NO: 1.

Figure 1A:
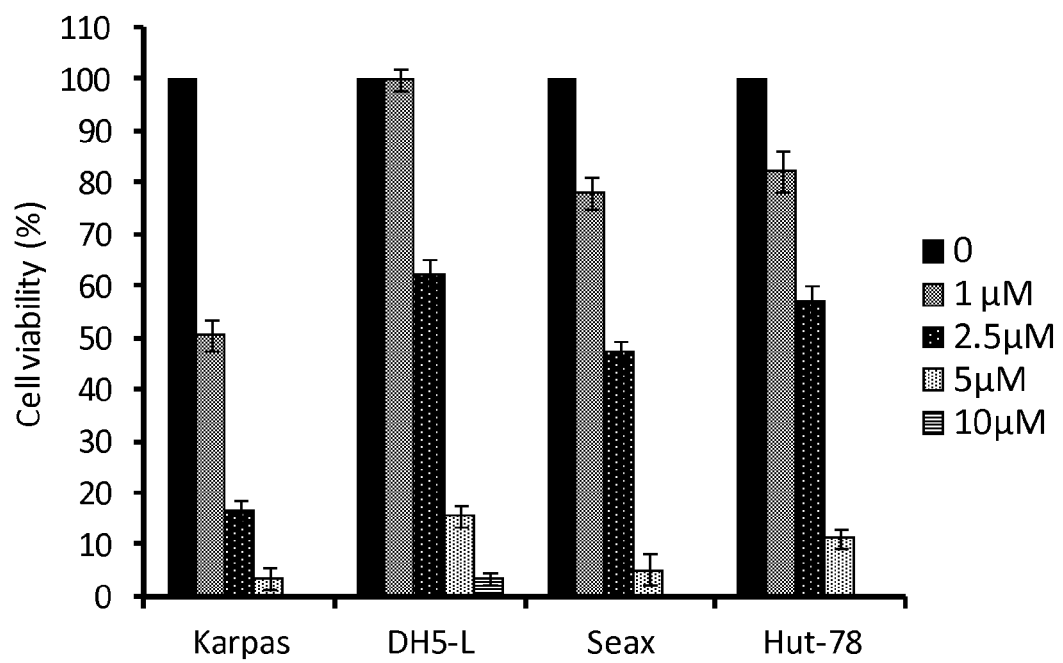

19 Claims, 13 Drawing Sheets
Specification includes a Sequence Listing.

METHODS AND PHARMACEUTICAL COMPOSITIONS FOR THE TREATMENT OF CANCER

FIELD OF THE INVENTION

The present invention relates to methods and pharmaceutical compositions for the treatment of cancer.

BACKGROUND OF THE INVENTION

Cancer treatments which target several pathways within cancer cells have been developed recently. However, some type of cancers exhibit different known or unknown pathway disruptions or develop treatment resistance. Thus, these cancer treatments are limited since they do not cause cell death in these types of cancer cells and are ineffective at treating various type of cancer.

Accordingly, there is a need to develop new approaches and drugs that will be suitable for effective and efficient treatment of cancer and targeting various type of cancer. In this way, it has been suggested that characterization of new therapeutic compounds in cancer inducing cell death through membranolysis of cancer cells may be highly desirable.

AAC-11 is an antiapoptotic protein (antiapoptosis clone 11) (Tewari et al., 1997), also called Api5 or FIF (Morris et al., 2006; Van den Berghe et al., 2000). AAC-11 is a nuclear protein whose expression has been demonstrated to prevent apoptosis following growth factor deprivation (Kim et al., 2000; Tewari et al., 1997). AAC-11 antiapoptotic action appears by the suppression of the transcription factor E2F1-induced apoptosis (Morris et al., 2006). The AAC-11 gene has been shown to be highly expressed in multiple cancer cell lines as well as in some metastatic lymph node tissues and in B cell chronic lymphoid leukemia (Clegg et al., 2003; Kim et al., 2000; Krejci et al., 2007; Morris et al., 2006; Sasaki et al., 2001; Tewari et al., 1997; Van den Berghe et al., 2000). AAC-11 expression seems to confer a poor outcome in subgroups of patients with non-small cell lung carcinoma whereas its depletion appears to be tumor cell lethal under condition of low-serum stress (Krejci et al., 2007; Sasaki et al., 2001). Interestingly, AAC-11 overexpression has been reported to promote both cervical cancer cells growth and invasiveness (Kim et al., 2000). Combined, these observations implicate AAC-11 as a putative metastatic oncogene.

There is no disclosure in the art of AAC-11-LZ-derived peptide effects in cancer, the induction of a rapid cell death through membranolysis of cancer cells and the use of the AAC-11-LZ-derived peptide in the treatment of cancer, and the prevention of metastasis in metastatic cancer.

SUMMARY OF THE INVENTION

The present invention relates to methods and pharmaceutical compositions for the treatment of cancer.

DETAILED DESCRIPTION OF THE INVENTION

The inventors demonstrated that some peptides derived from the AAC-11 protein selectively disrupt vital cellular functions in a plurality of cancer cells, at micromolar range. In particular, the inventors surprisingly found that the peptides specifically target the plasma membrane of cancer cells. Without to be bound by any theory, the peptides probably bind to a specific partner present in the cancer cell membrane. This binding could allow the peptides to remain in the membrane where it could undergo pore formation, as described for other membrane-active peptides. The inventors also demonstrate that under low serum conditions, the peptides induce a rapid cell death through membranolysis of cancer cells. Finally, the inventors demonstrate that the peptides inhibit cell migration and invasion. In vivo studies using mouse tumor models indicate that these peptides inhibit tumor growth in nude mice bearing human non-small cell lung cancer A549 subcutaneous xenografts and nude mice bearing subcutaneous triple-negative breast tumor xenografts derived from patient biopsies. In an acute promyelocytic leukemia (APL) mouse model, the peptides exhibited a pronounced effect on mice survival. Because AAC-11 peptides-induced cell death is independent of the tumour suppressor p53 status, such a strategy may have a wide spectrum of therapeutic activity. Thus, the inventors report herein novel anti-cancer peptides that impair cell migration and invasion and specifically induce tumor cell death and offer promising therapeutic potential.

AAC-11-LZ-derived Peptides

The present invention provides isolated, synthetic or recombinant AAC-11 leucine-zipper (LZ) derived peptides ("AAC-11-LZ-derived peptides").

As used herein the term "AAC-11" has its general meaning in the art and refers to the antiapoptosis clone 11 protein that is also known as Api5 or FIF. An exemplary human polypeptide sequence of AAC-11 is deposited in the GenBank database accession number: Q9BZZ5 set forth as SEQ ID NO:1.

```
SEQ ID NO: 1 for AAC-11 Q9BZZ5
MPTVEELYRNYGILADATEQVGQHKDAYQVILDGVKGGTKEKRLAAQFIP

KFFKHFPELADSAINAQLDLCEDEDVSIRRQAIKELPQFATGENLPRVAD

ILTQLLQTDDSAEFNLVNNALLSIFKMDAKGTLGGLFSQILQGEDIVRER

AIKFLSTKLKTLPDEVLTKEVEELILTESKKVLEDVTGEEFVLFMKILSG

LKSLQTVSGRQQLVELVAEQADLEQTFNPSDPDCVDRLLQCTRQAVPLFS

KNVHSTRFVTYFCEQVLPNLGTLTTPVEGLDIQLEVLKLLAEMSSFCGDM

EKLETNLRKLFDKLLEYMPLPPEEAENGENAGNEEPKLQFSYVECLLYSF

HQLGRKLPDFLTAKLNAEKLKDFKIRLQYFARGLQVYIRQLRLALQGKTG

EALKTEENKIKVVALKITNNINVLIKDLFHIPPSYKSTVTLSWKPVQKVE

IGQKRASEDTTSGSPPKKSSAGPKRDARQIYNPPSGKYSSNLGNFNYEQR

GAFRGSRGGRGWGTRGNRSRGRLY
```

The present invention relates to a polypeptide comprising or consisting of i) an amino acid sequence ranging from the phenylalanine residue at position 380 to the leucine residue at position 384 in SEQ ID NO:1 or, ii) an amino acid sequence having at least 70% of identity with the amino acid sequence ranging from the phenylalanine residue at position 380 to the leucine residue at position 384 in SEQ ID NO:1, or iii) an amino acid sequence which is a retro-inverso of the amino acid sequence ranging from the phenylalanine residue at position 380 to the leucine residue at position 384 in SEQ ID NO:1 or, iv) an amino acid sequence which is retro-inverso of the amino acid sequence having at least 70% of identity with the amino acid sequence ranging from the phenylalanine residue at position 380 to the leucine residue at position 384 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In a particular embodiment, the polypeptide comprises or consists of i) an amino acid sequence ranging from the phenylalanine residue at position 380 to the isoleucine residue at position 388 in SEQ ID NO:1 or, ii) an amino acid sequence having at least 70% of identity with the amino acid sequence ranging from the phenylalanine residue at position 380 to the isoleucine residue at position 388 in SEQ ID NO:1, or iii) an amino acid sequence which is a retro-inverso of the amino acid sequence ranging from the phenylalanine residue at position 380 to the isoleucine residue at position 388 in SEQ ID NO:1 or, iv) an amino acid sequence which is retro-inverso of the amino acid sequence having at least 70% of identity with the amino acid sequence ranging from the phenylalanine residue at position 380 to the isoleucine residue at position 388 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In a particular embodiment, the polypeptide comprises or consists of i) an amino acid sequence ranging from the phenylalanine residue at position 380 to the leucine residue at position 391 in SEQ ID NO:1 or, ii) an amino acid sequence having at least 70% of identity with the amino acid sequence ranging from the phenylalanine residue at position 380 to the leucine residue at position 391 in SEQ ID NO:1, or iii) an amino acid sequence which is a retro-inverso of the amino acid sequence ranging from the phenylalanine residue at position 380 to the leucine residue at position 391 in SEQ ID NO:1 or, iv) an amino acid sequence which is retro-inverso of the amino acid sequence having at least 70% of identity with the amino acid sequence ranging from the phenylalanine residue at position 380 to the leucine residue at position 391 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In a particular embodiment, the polypeptide comprises or consists of i) an amino acid sequence ranging from the tyrosine residue at position 379 to the leucine residue at position 391 in SEQ ID NO:1 or, ii) an amino acid sequence having at least 70% of identity with the amino acid sequence ranging from the tyrosine residue at position 379 to the leucine residue at position 391 in SEQ ID NO:1, or iii) an amino acid sequence which is a retro-inverso of the amino acid sequence ranging from the tyrosine residue at position 379 to the leucine residue at position 391 in SEQ ID NO:1 or, iv) an amino acid sequence which is retro-inverso having at least 70% of identity with the amino acid sequence ranging from the tyrosine residue at position 379 to the leucine residue at position 391 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In a particular embodiment, the polypeptide comprises or consists of i) an amino acid sequence ranging from the glutamine residue at position 378 to the leucine residue at position 391 in SEQ ID NO:1 or, ii) an amino acid sequence having at least 70% of identity with the amino acid sequence ranging from glutamine residue at position 378 to the leucine residue at position 391 in SEQ ID NO:1, or iii) an amino acid sequence which is a retro-inverso of the amino acid sequence ranging from glutamine residue at position 378 to the leucine residue at position 391 in SEQ ID NO:1 or, iv) an amino acid sequence which is retro-inverso having at least 70% of identity with the amino acid sequence ranging from glutamine residue at position 378 to the leucine residue at position 391 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In a particular embodiment, the polypeptides comprises or consists of i) an amino acid sequence ranging from the leucine residue at position 377 to the leucine residue at position 391 in SEQ ID NO:1 or, ii) an amino acid sequence having at least 70% of identity with the amino acid sequence ranging from the leucine residue at position 377 to the leucine residue at position 391 in SEQ ID NO:1, or iii) an amino acid sequence which is a retro-inverso of the amino acid sequence ranging from the leucine residue at position 377 to the leucine residue at position 391 in SEQ ID NO:1 or, iv) an amino acid sequence which is retro-inverso having at least 70% of identity with the amino acid sequence ranging from the leucine residue at position 377 to the leucine residue at position 391 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In some embodiment, the polypeptide comprises or consists of i) an amino acid sequence ranging from the lysine residue at position 371 to the glycine residue at position 397 in SEQ ID NO:1 or, ii) an amino acid sequence having at least 70% of identity with the amino acid sequence ranging from the lysine residue at position 371 to the glycine residue at position 397 in SEQ ID NO:1, or iii) an amino acid sequence which is a retro-inverso of the amino acid sequence ranging from the lysine residue at position 371 to the glycine residue at position 397 in SEQ ID NO:1 or, iv) an amino acid sequence which is retro-inverso having at least 70% of identity with the amino acid sequence ranging from the lysine residue at position 371 to the glycine residue at position 397 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In some embodiment, the polypeptides comprises or consists of i) an amino acid sequence ranging from the lysine residue at position 371 to the leucine residue at position 391 in SEQ ID NO:1 or, ii) an amino acid sequence having at least 70% of identity with the amino acid sequence ranging from the lysine residue at position 371 to the leucine residue at position 391 in SEQ ID NO:1, or iii) an amino acid sequence which is a retro-inverso of the amino acid sequence ranging from the lysine residue at position 371 to the leucine residue at position 391 in SEQ ID NO:1 or, iv) an amino acid sequence which is retro-inverso having at least 70% of identity with the amino acid sequence ranging from the lysine residue at position 371 to the leucine residue at position 391 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In some embodiment, the polypeptide comprises or consists of i) an amino acid sequence ranging from the phenylalanine residue at position 380 to the threonine residue at position 399 in SEQ ID NO:1 or, ii) an amino acid sequence having at least 70% of identity with the amino acid sequence ranging from the phenylalanine residue at position 380 to the threonine residue at position 399 in SEQ ID NO:1, or iii) an amino acid sequence which is a retro-inverso of the amino acid sequence ranging from the phenylalanine residue at position 380 to the threonine residue at position 399 in SEQ ID NO:1 or, iv) an amino acid sequence which is retro-inverso having at least 70% of identity with the amino acid sequence ranging from the phenylalanine residue at position 380 to the threonine residue at position 399 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In some embodiment, the polypeptide comprises or consists of i) an amino acid sequence ranging from the lysine residue at position 371 to the threonine residue at position 399 in SEQ ID NO:1 or, ii) an amino acid sequence having at least 70% of identity with the amino acid sequence ranging from the lysine residue at position 371 to the threonine residue at position 399 in SEQ ID NO:1, or iii) an amino acid sequence which is a retro-inverso of the amino acid sequence ranging from the lysine residue at position 371 to the threonine residue at position 399 in SEQ ID NO:1 or, iv) an amino acid sequence which is retro-inverso having at least 70% of identity with the amino acid sequence ranging from the lysine residue at position 371 to the threonine residue at position 399 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

In some embodiment, the polypeptide comprises or consists of i) an amino acid sequence ranging from the leucine residue at position 377 to the threonine residue at position 399 in SEQ ID NO:1 or, ii) an amino acid sequence having at least 70% of identity with the amino acid sequence ranging from the leucine residue at position 377 to the threonine residue at position 399 in SEQ ID NO:1, or iii) an amino acid sequence which is a retro-inverso of the amino acid sequence ranging from the leucine residue at position 377 to the threonine residue at position 399 in SEQ ID NO:1 or, iv) an amino acid sequence which is retro-inverso having at least 70% of identity with the amino acid sequence ranging from the leucine residue at position 377 to the threonine residue at position 399 in SEQ ID NO:1, wherein the polypeptide does not consist of the amino acid sequence SEQ ID NO:1 and does not consist of the amino acid sequence ranging from the alanine residue at position 363 to the threonine residue at position 399 in SEQ ID NO:1.

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence. Amino acid sequence identity is preferably determined using a suitable sequence alignment algorithm and default parameters, such as BLAST P (Karlin and Altschul, 1990).

The term "retro-inverso amino acid sequence" relates to an isomeric form of an amino acid sequence in which the direction of the amino acid sequence is reversed and the chirality of each amino acid residue is inverted. Retro-inverso amino acid sequence of the present invention may be composed by D-amino acids assembled in the reverse order from that of the parental amino acid sequence-sequence.

In some embodiments, the polypeptide of the invention comprises 5, 6, 7, 8, 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100 amino acids. In some embodiments, the polypeptide of the invention comprises less than 50 amino acids. In some embodiments, the polypeptide of the invention comprises less than 30 amino acids. In some embodiments, the polypeptide of the invention comprises less than 25 amino acids. In some embodiments, the polypeptide of the invention comprises less than 20 amino acids. In some embodiments, the polypeptide of the invention comprises less than 15 amino acids.

Fusion Proteins of the Invention

A further aspect of the present invention relates to a fusion protein comprising a polypeptide according to the invention that is fused to at least one heterologous polypeptide.

The term "fusion protein" refers to the polypeptide according to the invention that is fused directly or via a spacer to at least one heterologous polypeptide.

According to the invention, the fusion protein comprises the polypeptide according to the invention that is fused either directly or via a spacer at its C-terminal end to the N-terminal end of the heterologous polypeptide, or at its N-terminal end to the C-terminal end of the heterologous polypeptide.

As used herein, the term "directly" means that the (first or last) amino acid at the terminal end (N or C-terminal end) of the polypeptide is fused to the (first or last) amino acid at the terminal end (N or C-terminal end) of the heterologous polypeptide.

In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide.

As used herein, the term "spacer" refers to a sequence of at least one amino acid that links the polypeptide of the invention to the heterologous polypeptide. Such a spacer may be useful to prevent steric hindrances.

In some embodiments, the heterologous polypeptide is a cell-penetrating peptide, a Transactivator of Transcription (TAT) cell penetrating sequence, a cell permeable peptide or a membranous penetrating sequence.

The term "cell-penetrating peptides" are well known in the art and refers to cell permeable sequence or membranous penetrating sequence such as penetratin, TAT mitochondrial penetrating sequence and compounds (Bechara and Sagan, 2013; Jones and Sayers, 2012; Khafagy el and Morishita, 2012; Malhi and Murthy, 2012).

In a particular embodiment, the heterologous polypeptide is an internalization sequence derived either from the homeodomain of *Drosophila* Antennapedia/Penetratin (Antp) protein (amino acids 43-58; SEQ ID NO:2) or the Transactivator of Transcription (TAT) cell penetrating sequences (SEQ ID NO:12).

In a particular embodiment, one, two or three glycine residue are added at the C-terminal end of the TAT cell penetrating sequences (SEQ ID NO:12).

In some embodiments, the fusion protein of the present invention comprises or consists of a sequence selected from the group consisting of SEQ ID NO:4, SEQ ID NO:6; SEQ ID NO:7, SEQ ID NO:8, SEQ ID NO:9, SEQ ID NO:10; SEQ ID NO:11; SEQ ID NO:13; SEQ ID NO:14; SEQ ID NO:16; and SEQ ID NO:17.

In another embodiment, the heterologous polypeptide is a cancer therapeutic polypeptide.

The term "cancer therapeutic polypeptide" refers to any polypeptide that has anti-cancer activities (e.g., proliferation inhibiting, growth inhibiting, apoptosis inducing, metastasis inhibiting, adhesion inhibiting, neovascularization inhibiting). Several such polypeptides are known in the art. (See. e.g., (Boohaker et al., 2012; Choi et al., 2011; Janin, 2003; Li et al., 2013; Sliwkowski and Mellman, 2013)).

In some embodiment, the heterologous polypeptide is a tumor targeting agent.

Tumor targeting agent include but are not limited to antibodies directed against the EDB domain of fibronectin, antibodies or agents binding Vascular endothelial growth factor receptor 2, antibodies or molecules binding fibroblast growth factor receptor-1, antibodies or agents that interact with CD31, antibodies or agents interacting with tumor lymphatic endothelium (Podoplanin, Lyve-1), or antibodies or agents binding to αVβ3 integrin such as RGD peptides, or antibodies or agents interacting with tumor membrane-bound and intracellular targets.

Polypeptides and Fusion Proteins Production

The polypeptides or fusion proteins of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides or fusion proteins, by standard techniques for production of amino acid sequences. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides or fusion proteins of the invention can be synthesized by recombinant DNA techniques as is now well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

Polypeptides or fusion proteins of the invention can be used in an isolated (e.g., purified) form or contained in a vector, such as a membrane or lipid vesicle (e.g. a liposome).

In specific embodiments, it is contemplated that polypeptides or fusion proteins according to the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

For example, Pegylation is a well-established and validated approach for the modification of a range of polypeptides (Chapman, 2002). The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein (Cunningham-Rundles et.

al., 1992); and (e) improved thermal and mechanical stability of the PEGylated polypeptide.

Therefore, advantageously, the polypeptides of the invention may be covalently linked with one or more polyethylene glycol (PEG) group(s). One skilled in the art can select a suitable molecular mass for PEG, based on how the pegylated polypeptide will be used therapeutically by considering different factors including desired dosage, circulation time, resistance to proteolysis, immunogenicity, etc.

In one embodiment, the PEG of the invention terminates on one end with hydroxy or methoxy, i.e., X is H or $CH_3$ ("methoxy PEG"). In addition, such a PEG can consist of one or more PEG side-chains which are linked together. PEGs with more than one PEG chain are called branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. One form of PEGs includes two PEG side-chains (PEG2) linked via the primary amino groups of a lysine (Monfardini et al., 1995).

To effect covalent attachment of PEG groups to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPDX-PEG, NCO-PEG, NPC-PEG, CDI-PEG, ALD-PEG, TRES-PEG, VS-PEG, IODO-PEG, and MAL-PEG, and branched PEGs such as PEG2-NHS.

The conjugation of the polypeptides or fusion proteins and the activated polymer molecules is conducted by use of any conventional method. Conventional methods are known to the skilled artisan. The skilled person will be aware that the activation method and/or conjugation chemistry to be used depends on the attachment group(s) of the polypeptides as well as the functional groups of the PEG molecule (e.g., being amine, hydroxyl, carboxyl, aldehyde, ketone, sulfhydryl, succinimidyl, maleimide, vinylsulfone or haloacetate).

In one embodiment, polypeptides are conjugated with PEGs at amino acid D and E (for COOH), T, Y and S (for OH), K (for $NH_2$), C (for SH if at least one cysteine is conserved) or/and Q and N (for the amide function).

In one embodiment, additional sites for PEGylation can be introduced by site-directed mutagenesis by introducing one or more lysine residues. For instance, one or more arginine residues may be mutated to a lysine residue. In another embodiment, additional PEGylation sites are chemically introduced by modifying amino acids on polypeptides of the invention.

In one embodiment, PEGs are conjugated to the polypeptides or fusion proteins through a linker. Suitable linkers are well known to the skilled person. A preferred example is cyanuric chloride ((Abuchowski et al., 1977); U.S. Pat. No. 4,179,337).

Conventional separation and purification techniques known in the art can be used to purify pegylated polypeptides of the invention, such as size exclusion (e.g. gel filtration) and ion exchange chromatography. Products may also be separated using SDS-PAGE.

In one embodiment, the pegylated polypeptides provided by the invention have a serum half-life in vivo at least 50%, 75%, 100%, 150% or 200% greater than that of an unmodified polypeptide.

Nucleic Acids, Vectors and Recombinant Host Cells

A further object of the present invention relates to a nucleic acid sequence encoding for a polypeptide or a fusion protein according to the invention.

As used herein, a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid sequences can be obtained by conventional methods well known to those skilled in the art.

Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule encoding for a polypeptide or a fusion protein of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Any expression vector for animal cell can be used. Examples of suitable vectors include pAGE107 (Miyaji et al., 1990), pAGE103 (Mizukami and Itoh, 1987), pHSG274 (Brady et al., 1984), pKCR (O'Hare et al., 1981), pSG1 beta d2-4 (Miyaji et al., 1990) and the like.

Other examples of plasmids include replicating plasmids comprising an origin of replication, or integrative plasmids, such as for instance pUC, pcDNA, pBR, and the like.

Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

Examples of promoters and enhancers used in the expression vector for animal cell include early promoter and enhancer of SV40 (Mizukami and Itoh, 1987), LTR promoter and enhancer of Moloney mouse leukemia virus (Kuwana et al., 1987), promoter (Mason et al., 1985) and enhancer (Gillies et al., 1983) of immunoglobulin H chain and the like.

A further aspect of the invention relates to a host cell comprising a nucleic acid molecule encoding for a polypeptide or a fusion protein according to the invention or a vector according to the invention. In particular, a subject of the present invention is a prokaryotic or eukaryotic host cell genetically transformed with at least one nucleic acid molecule or vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In a particular embodiment, for expressing and producing polypeptides or fusion proteins of the invention, prokaryotic cells, in particular *E. coli* cells, will be chosen. Actually, according to the invention, it is not mandatory to produce the polypeptide or the fusion protein of the invention in a eukaryotic context that will favour post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the fusion protein of the invention.

The construction of expression vectors in accordance with the invention, and the transformation of the host cells can be carried out using conventional molecular biology techniques. The polypeptide or the fusion protein of the invention, can, for example, be obtained by culturing genetically transformed cells in accordance with the invention and recovering the polypeptide or the fusion protein expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the proteins in accordance with the invention.

A further aspect of the invention relates to a method for producing a polypeptide or a fusion protein of the invention comprising the step consisting of: (i) culturing a transformed host cell according to the invention under conditions suitable to allow expression of said polypeptide or fusion protein; and (ii) recovering the expressed polypeptide or fusion protein.

Therapeutic Methods and Uses

The polypeptide or the fusion protein of the invention may be used in a method of treating cancer in a subject in need thereof.

Therefore, a further aspect of the invention relates to the polypeptide or the fusion protein of the invention for use as a medicament.

In one embodiment, the present invention relates to the polypeptide or the fusion protein of the invention for use in the treatment of cancer in a subject in need thereof.

As used herein, the term "subject" denotes a mammal, such as a rodent, a feline, a canine, and a primate. Preferably a subject according to the invention is a human. Preferably a subject according to the invention is a subject afflicted or susceptible to be afflicted with a cancer.

As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the cancer is selected from the group consisting of breast cancer, triple-negative breast cancer, Acute Promyelocytic Leukemia (AML), hematologic cancer, lymphoma, B cell lymphoma, T cell lymphoma, B-cell non-Hodgkin's lymphoma, T-acute lymphoblastic leukemia, lung adenocarcinoma, kidney cancer, ovarian carcinoma, colon carcinoma, melanoma, Sezary syndrome.

In one embodiment, the present invention relates to the polypeptide comprising or consisting of
  i) an amino acid sequence ranging from the phenylalanine residue at position 380 to the leucine residue at position 384 in SEQ ID NO:1 or,
  ii) an amino acid sequence having at least 70% of identity with the amino acid sequence ranging from the phenylalanine residue at position 380 to the leucine residue at position 384 in SEQ ID NO:1, or
  iii) an amino acid sequence which is a retro-inverso of the amino acid sequence ranging from the phenylalanine residue at position 380 to the leucine residue at position 384 in SEQ ID NO:1 or,
  iv) an amino acid sequence which is retro-inverso of the amino acid sequence having at least 70% of identity with the amino acid sequence ranging from the phenylalanine residue at position 380 to the leucine residue at position 384 in SEQ ID NO:1,
  wherein the polypeptide does not consist of the amino acid sequence SEQ ID NO:1 for use in the treatment of cancer in a subject in need thereof.

In a particular embodiment, the present invention relates to the polypeptide comprising or consisting of
  i) an amino acid sequence ranging from the phenylalanine residue at position 380 to the isoleucine residue at position 388 in SEQ ID NO:1 or,
  ii) an amino acid sequence having at least 70% of identity with the amino acid sequence ranging from the phenylalanine residue at position 380 to the isoleucine residue at position 388 in SEQ ID NO:1, or
  iii) an amino acid sequence which is a retro-inverso of the amino acid sequence ranging from the phenylalanine residue at position 380 to the isoleucine residue at position 388 in SEQ ID NO:1 or,
  iv) an amino acid sequence which is retro-inverso of the amino acid sequence having at least 70% of identity with the amino acid sequence ranging from the phenylalanine residue at position 380 to the isoleucine residue at position 388 in SEQ ID NO:1,
  wherein the polypeptide does not consist of the amino acid sequence SEQ ID NO:1 for use in the treatment of cancer in a subject in need thereof.

In a particular embodiment, the present invention relates to the polypeptide comprising or consisting of
  i) an amino acid sequence ranging from the phenylalanine residue at position 380 to the leucine residue at position 391 in SEQ ID NO:1 or,
  ii) an amino acid sequence having at least 70% of identity with the amino acid sequence ranging from the phenylalanine residue at position 380 to the leucine residue at position 391 in SEQ ID NO:1, or
  iii) an amino acid sequence which is a retro-inverso of the amino acid sequence ranging from the phenylalanine residue at position 380 to the leucine residue at position 391 in SEQ ID NO:1 or,
  iv) an amino acid sequence which is retro-inverso of the amino acid sequence having at least 70% of identity with the amino acid sequence ranging from the phenylalanine residue at position 380 to the leucine residue at position 391 in SEQ ID NO:1,
  wherein the polypeptide does not consist of the amino acid sequence SEQ ID NO:1 for use in the treatment of cancer in a subject in need thereof.

In a particular embodiment, the present invention relates to the polypeptide comprising or consisting of
  i) an amino acid sequence ranging from the tyrosine residue at position 379 to the leucine residue at position 391 in SEQ ID NO:1 or,
  ii) an amino acid sequence having at least 70% of identity with the amino acid sequence ranging from the tyrosine residue at position 379 to the leucine residue at position 391 in SEQ ID NO:1, or
  iii) an amino acid sequence which is a retro-inverso of the amino acid sequence ranging from the tyrosine residue at position 379 to the leucine residue at position 391 in SEQ ID NO:1 or,
  iv) an amino acid sequence which is retro-inverso having at least 70% of identity with the amino acid sequence ranging from the tyrosine residue at position 379 to the leucine residue at position 391 in SEQ ID NO:1,
  wherein the polypeptide does not consist of the amino acid sequence SEQ ID NO:1 for use in the treatment of cancer in a subject in need thereof.

In a particular embodiment, the present invention relates to the polypeptide comprising or consisting of
  i) an amino acid sequence ranging from the glutamine residue at position 378 to the leucine residue at position 391 in SEQ ID NO:1 or,
  ii) an amino acid sequence having at least 70% of identity with the amino acid sequence ranging from glutamine residue at position 378 to the leucine residue at position 391 in SEQ ID NO:1, or
  iii) an amino acid sequence which is a retro-inverso of the amino acid sequence ranging from glutamine residue at position 378 to the leucine residue at position 391 in SEQ ID NO:1 or, iv) an amino acid sequence which is retro-inverso having at least 70% of identity with the amino acid sequence ranging from glutamine residue at position 378 to the leucine residue at position 391 in SEQ ID NO:1, wherein the polypeptide does not consist of the amino acid sequence SEQ ID NO:1 for use in the treatment of cancer in a subject in need thereof.

In a particular embodiment, the present invention relates to the polypeptide comprising or consisting of i) an amino acid sequence ranging from the leucine residue at position 377 to the leucine residue at position 391 in SEQ ID NO:1 or, ii) an amino acid sequence having at least 70% of identity with the amino acid sequence ranging from the leucine residue at position 377 to the leucine residue at position 391 in SEQ ID NO:1, or iii) an amino acid sequence which is a retro-inverso of the amino acid sequence ranging from the leucine residue at position 377 to the leucine residue at position 391 in SEQ ID NO:1 or, iv) an amino acid sequence which is retro-inverso having at least 70% of identity with the amino acid sequence ranging from the leucine residue at position 377 to the leucine residue at position 391 in SEQ ID NO:1, wherein the polypeptide does not consist of the amino acid sequence SEQ ID NO:1 for use in the treatment of cancer in a subject in need thereof.

In some embodiment, the present invention relates to the polypeptide comprising or consisting of i) an amino acid sequence ranging from the lysine residue at position 371 to the glycine residue at position 397 in SEQ ID NO:1 or, ii) an amino acid sequence having at least 70% of identity with the amino acid sequence ranging from the lysine residue at position 371 to the glycine residue at position 397 in SEQ ID NO:1, or iii) an amino acid sequence which is a retro-inverso of the amino acid sequence ranging from the lysine residue at position 371 to the glycine residue at position 397 in SEQ ID NO:1 or, iv) an amino acid sequence which is retro-inverso having at least 70% of identity with the amino acid sequence ranging from the lysine residue at position 371 to the glycine residue at position 397 in SEQ ID NO:1, wherein the polypeptide does not consist of the amino acid sequence SEQ ID NO:1 for use in the treatment of cancer in a subject in need thereof.

In some embodiment, the present invention relates to the polypeptide comprising or consisting of i) an amino acid sequence ranging from the lysine residue at position 371 to the leucine residue at position 391 in SEQ ID NO:1 or, ii) an amino acid sequence having at least 70% of identity with the amino acid sequence ranging from the lysine residue at position 371 to the leucine residue at position 391 in SEQ ID NO:1, or iii) an amino acid sequence which is a retro-inverso of the amino acid sequence ranging from the lysine residue at position 371 to the leucine residue at position 391 in SEQ ID NO:1 or, iv) an amino acid sequence which is retro-inverso having at least 70% of identity with the amino acid sequence ranging from the lysine residue at position 371 to the leucine residue at position 391 in SEQ ID NO:1, wherein the polypeptide does not consist of the amino acid sequence SEQ ID NO:1 for use in the treatment of cancer in a subject in need thereof.

In some embodiment, the present invention relates to the polypeptide comprising or consisting of i) an amino acid sequence ranging from the phenylalanine residue at position 380 to the threonine residue at position 399 in SEQ ID NO:1 or, ii) an amino acid sequence having at least 70% of identity with the amino acid sequence ranging from the phenylalanine residue at position 380 to the threonine residue at position 399 in SEQ ID NO:1, or iii) an amino acid sequence which is a retro-inverso of the amino acid sequence ranging from the phenylalanine residue at position 380 to the threonine residue at position 399 in SEQ ID NO:1 or, iv) an amino acid sequence which is retro-inverso having at least 70% of identity with the amino acid sequence ranging from the phenylalanine residue at position 380 to the threonine residue at position 399 in SEQ ID NO:1, wherein the polypeptide does not consist of the amino acid sequence SEQ ID NO:1 for use in the treatment of cancer in a subject in need thereof.

In some embodiment, the present invention relates to the polypeptide comprising or consisting of i) an amino acid sequence ranging from the lysine residue at position 371 to the threonine residue at position 399 in SEQ ID NO:1 or, ii) an amino acid sequence having at least 70% of identity with the amino acid sequence ranging from the lysine residue at position 371 to the threonine residue at position 399 in SEQ ID NO:1, or iii) an amino acid sequence which is a retro-inverso of the amino acid sequence ranging from the lysine residue at position 371 to the threonine residue at position 399 in SEQ ID NO:1 or, iv) an amino acid sequence which is retro-inverso having at least 70% of identity with the amino acid sequence ranging from the lysine residue at position 371 to the threonine residue at position 399 in SEQ ID NO:1, wherein the polypeptide does not consist of the amino acid sequence SEQ ID NO:1 for use in the treatment of cancer in a subject in need thereof.

In some embodiment, the present invention relates to the polypeptide comprising or consisting of i) an amino acid sequence ranging from the leucine residue at position 377 to the threonine residue at position 399 in SEQ ID NO:1 or, ii) an amino acid sequence having at least 70% of identity with the amino acid sequence ranging from the leucine residue at position 377 to the threonine residue at position 399 in SEQ ID NO:1, or iii) an amino acid sequence which is a retro-inverso of the amino acid sequence ranging from the leucine residue at position 377 to the threonine residue at position 399 in SEQ ID NO:1 or, iv) an amino acid sequence which is retro-inverso having at least 70% of identity with the amino acid sequence ranging from the leucine residue at position 377 to the threonine residue at position 399 in SEQ ID NO:1, wherein the polypeptide does not consist of the amino acid sequence SEQ ID NO:1 for use in the treatment of cancer in a subject in need thereof.

In one embodiment, the present invention relates to the polypeptide or the fusion protein of the invention for use in the prevention of metastasis in metastatic cancer.

In one embodiment, the present invention relates to the polypeptide or the fusion protein of the invention for use in a method of causing membranolysis in cancer cells in a subject in need thereof.

The term "membranolysis" refers to formation of pores in the cell membranes of the cancer cells, causing membranolysis, which allow for extrusion of the intracellular contents from the interior of the cancer cell, resulting in the compromise of the integrity of the cell. Once membranolysis starts, the cell eventually undergoes necrosis, or cell death, as a result of the treatment with the methods and compositions of the present invention.

In one embodiment, the present invention relates to the polypeptide or the fusion protein of the invention for use in enhancing therapeutic efficacy of cancer treatment in a subject in need thereof.

In a particular embodiment the polypeptide or the fusion protein of the invention may be administered sequentially or concomitantly with one or more therapeutic active agent such as chemotherapeutic or radiotherapeutic agents.

Examples of chemotherapeutics include but are not limited to fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, epipodophyllotoxins such as etoposide and teniposide, camptothecins such as irinotecan and topotecan, bleomycin, doxorubicin, idarubicin, daunorubicin, dactinomycin, plicamycin, mitoxantrone, L-asparaginase, doxorubicin, epirubicin, 5-fluorouracil and 5-fluorouracil combined with leucovorin, taxanes such as docetaxel and paclitaxel, levamisole, estramustine, nitrogen mustards, nitrosoureas such as carmustine and lomustine, vinca alkaloids such as vinblastine, vincristine, vindesine and vinorelbine, imatinib mesylate, hexamethylmelamine, kinase inhibitors, phosphatase inhibitors, ATPase inhibitors, tyrphostins, protease inhibitors, inhibitors herbimycin A, genistein, erbstatin, and lavendustin A. In one embodiment, additional therapeutic active agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxins, hormonal therapies, retinoids, photosensitizers or photodynamic therapies, angiogenesis inhibitors, antimitotic agents, isoprenylation inhibitors, cell cycle inhibitors, actinomycin, bleomycin, anthracyclines, MDR inhibitors and $Ca^{2+}$ ATPase inhibitors.

Additional therapeutic active agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Further therapeutic active agent can be an antiemetic agent. Suitable antiemetic agents include, but are not limited to, metoclopramide, domperidone, prochlorperazine, promethazine, chlorpromazine, trimethobenzamide, ondansetron, granisetron, hydroxyzine, acetylleucine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinols, thiethylperazine, thioproperazine and tropisetron. In a preferred embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, buprenorphine, meperidine, loperamide, ethoheptazine, betaprodine, diphenoxylate, fentanyl, sufentanil, alfentanil, remifentanil, levorphanol, dextromethorphan, phenazone, pemazocine, cyclazocine, methadone, isomethadone and propoxyphene. Suitable non-opioid analgesic agents include, but are not limited to, aspirin, celecoxib, rofecoxib, diclofenac, diflunisal, etodolac, fenoprofen, flurbiprofen, ibuprofen, ketoprofen, indomethacin, ketorolac, meclofenamate, mefenamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, clorazepate, clonazepam, chlordiazepoxide and alprazolam.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

Pharmaceutical Compositions

Another object of the invention relates to a pharmaceutical composition comprising the polypeptide or the fusion protein or the nucleic acid sequence or the expression vector or the host cell according to the invention and a pharmaceutically acceptable carrier.

Typically, the polypeptide or the fusion protein or the nucleic acid sequence or the expression vector or the host cell according to the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide or fusion protein of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The peptide or the fusion protein of the invention may be formulated within a therapeutic mixture to comprise about 0.0001 to 1.0 milligrams, or about 0.001 to 0.1 milligrams, or about 0.1 to 1.0 milligrams, or about 1 to 10 milligrams or even about 10 to 100 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Another object of the invention relates to a pharmaceutical composition according to the invention comprising one or more chemotherapeutic or radiotherapeutic agents.

The invention will be further illustrated by the following figures and examples. However, these examples and figures should not be interpreted in any way as limiting the scope of the present invention.

FIGURES

FIG. 1: Antp-AAC-11-LZ (363-399) peptide induced cell death. (A) Karpas 1106, SU-DHL-5, SeAx and HUT-78 cells were plated at a densities of $6 \times 10^3$ in 96 well plates (100 µL total volume per well) and treated for 24 hours in a 37° C. incubator (5% $CO_2$) with increasing concentrations of the Antp-AAC-11-LZ (363-399). 20 µL MTS reagent was then added to each well and plates were incubated for an additional 4 hours. Absorbance was measured at 490 nm using a 96-well plate reader. The extent to which the Antp-AAC-11-LZ (363-399) peptide inhibited cell proliferation was calculated as a percentage of the absorbance in each well containing the Antp-AAC-11-LZ (363-399) peptide relative to wells containing no peptide (negative control). Each bar represents the mean±s.d. from at least three independent experiments. (B) Indicated cells were plated at a densities of $4.5 \times 10^3$ in 96 well plates (100 µL total volume per well) and allowed to attach overnight in a 37° C. incubator (5% $CO_2$). Media was removed from cells and replaced with media containing Antp-AAC-11-LZ (363-399) peptide at various concentrations (100 µL total volume per well) peptide and the plates were incubated for 24 hours. The MTT assay was then completed and data analysis was performed as described herein. (C) Antp-AAC-11-LZ (363-399) peptide but not the mutant peptide Antp-AAC-11-LZ (363-399) L/G induced cell death under serum deprivation conditions. A549 cells were plated at a densities of $4.5\times10^3$ in 96 well plates (100 μL total volume per well) and allowed to attach overnight in a 37° C. incubator (5% $CO_2$). Media was removed from cells and replaced with media containing the indicated peptides at 10 μM (100 μL total volume per well) and the plates were incubated for 24 hours. The MTT assay was then completed and data analysis was performed as described herein.

FIG. 2: TAT-AAC-11-LZ (363-399), RI-TAT-AAC-11-LZ (363-399) and Cter-Antp-AAC-11-LZ (363-399) peptides preferentially kill tumor cells. (A) A549 cells were plated at a densities of $4.5\times10^3$ in 96 well plates (100 μL total volume per well) and allowed to attach overnight in a 37° C. incubator (5% $CO_2$). Media was removed from cells and replaced with media containing the indicated peptides at various concentrations (100 μL total volume per well) peptide in the absence of serum and the plates were incubated for 24 hours. The MTT assay was then completed and data analysis was performed as described herein. (B) A549 or HaCat cells were plated at a densities of $4.5\times10^3$ in 96 well plates (100 μL total volume per well) and allowed to attach overnight in a 37° C. incubator (5% $CO_2$). Media was removed from cells and replaced with media containing the indicated peptides at 10 μM (100 μL total volume per well) peptide in the absence of serum and the plates were incubated for 24 hours. The MTT assay was then completed and data analysis was performed as described herein.

Figure 3:
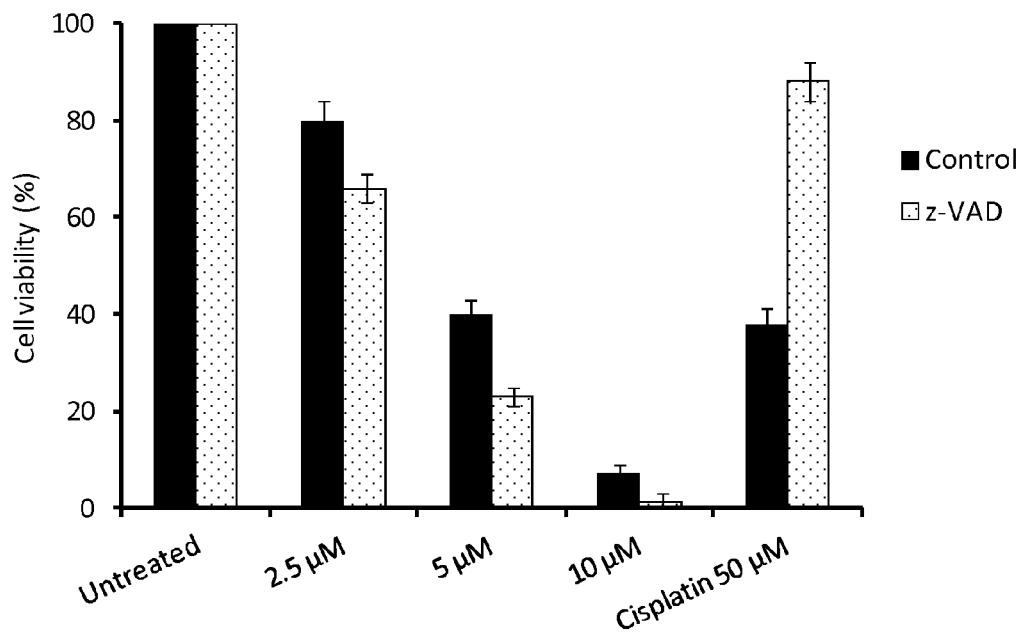

FIG. 3: Antp-AAC-11-LZ (363-399) peptide-induced cell death is not caspase-dependent apoptosis. A549 cells were plated at a densities of $4.5\times10^3$ in 96 well plates (100 μL total volume per well) and allowed to attach overnight in a 37° C. incubator (5% $CO_2$). Cells were left untreated or pre-treated with 100 μM Z-VAD-FMK for 2 h. Medium was removed from cells and replaced with medium containing Antp-AAC-11-LZ (363-399) peptide at various concentrations (100 μL total volume per well) or 50 μM cisplatin in the presence or in the absence of 100 μM Z-VAD-FMK and the plates were incubated for 24 hours. The MTT assay was then completed and data analysis was performed as described herein.

FIG. 4: Antp-AAC-11-LZ (363-399) peptide induced necrotic cell death under low serum conditions. (A) SeAx or HaCat cells cultured in the absence of 10% FBS were left untreated or treated with 4 μM or 10 μM, respectively, of the Antp-AAC-11-LZ (363-399) peptide for the indicated durations. Cells were then analyzed by flow cytometry for PI staining. The results represent the mean number of PI-positive cells±S.D. from at least three independent experiments. (B) A549 and HaCat cells were plated at a densities of $4.5\times10^3$ in 96 well plates (100 μL total volume per well) and allowed to attach overnight in a 37° C. incubator (5% $CO_2$). Media was removed from cells and replaced with media containing 10 μM Antp-AAC-11-LZ (363-399) peptide (100 μL total volume per well) peptide and the plates were incubated for the indicated durations. Lactate dehydrogenase (LDH) activity released in the culture medium was then assessed and data expressed as a percentage of the maximal level (Max) of LDH activity determined after total cell lysis±S.D. from at least three independent experiments.

FIG. 5: Antp-AAC-11 LZ peptides induced cell death. (A) A549 cells were plated at a densities of $4.5\times10^3$ in 96 well plates (100 μL total volume per well) and allowed to attach overnight in a 37° C. incubator (5% $CO_2$). Media was removed from cells and replaced with media containing the indicated Antp-AAC-11-LZ peptides at various concentrations (100 μL total volume per well) peptide and the plates were incubated for 24 hours. The MTT assay was then completed and data analysis was performed as described herein. (B) A549 or HaCat cells were plated at a densities of $4.5\times10^3$ in 96 well plates (100 μL total volume per well) and allowed to attach overnight in a 37° C. incubator (5% $CO_2$). Media was removed from cells and replaced with media containing the indicated peptides at 10 μM (100 μL total volume per well) peptide in the absence of serum and the plates were incubated for 24 hours. The MTT assay was then completed and data analysis was performed as described herein.

FIG. 6: Antp-AAC-11-LZ peptides induced necrotic cell death under low serum conditions. (A) SeAx cultured in the absence of 10% FBS were left untreated or treated with 4 μM of the indicated Antp-AAC-11-LZ peptides for various times. Cells were then analyzed by flow cytometry for PI staining. The results represent the mean number of PI-positive cells±S.D. (B) A549 cells were plated at a densities of $4.5\times10^3$ in 96 well plates (100 μL total volume per well) and allowed to attach overnight in a 37° C. incubator (5% $CO_2$). Media was removed from cells and replaced with media containing the indicated Antp-AAC-11-LZ peptides at 10 μM (100 μL total volume per well) peptide and the plates were incubated for the indicated durations. Lactate dehydrogenase (LDH) activity released in the culture medium was then assessed and data expressed as a percentage of the maximal level (Max) of LDH activity determined after total cell lysis±S.D.

FIG. 7: Antp-AAC-11-LZ (363-399) peptide inhibits cell migration and invasion. (A) D3H2LN cells were added to the upper well of modified Boyden chamber (transwell) plates with a vehicle or with either 2 μM of the Antp-AAC-11-LZ (363-399) peptide or the Antp-only peptide and subjected to a transwell migration assay as described under Materials and methods. The cells were allowed to migrate toward 10% FBS for 12 □h. Triplicate wells were used for each of three independent experiments. The results are expressed relative to the migration of the untreated cells (=100%). Column: Mean of three experiments. Bar: s.e. P-value was determined by Student's t-test (*P<0.01). (B) D3H2LN cells were seeded in a Matrigel-coated Boyden chamber with a vehicle or with either 2 μM of the Antp-AAC-11-LZ (363-399) peptide or the Antp-only peptide and subjected to a transwell migration assay as described under Materials and methods. The cells were allowed to migrate toward 10% FBS for 24 □h. Triplicate wells were used for each of three independent experiments. The results are expressed relative to the migration of the untreated cells (=100%). Column: Mean of three experiments. Bar: s.e. P-value was determined by Student's t-test (*P<0.01)

FIG. 8: (A) Effect of the Antp-AAC-11-LZ (363-399) peptide injection on body weight. Nude mice were injected intraperitoneally twice a week for 4 weeks with normal saline solution or the indicated doses of Antp-AAC-11-LZ (363-399) peptide (n=3-4 mice per group) and were monitored daily for body weight (mean±s.e.m). (B) Reduction of tumor growth in mouse models of triple-negative breast cancer as a result of systemic administration of the Antp-AAC-11-LZ (363-399) peptide. Two human triple-negative breast cancer xenografts (PDX01 and PDX02) were implanted into nude mice for experimentation. Once tumors reached a mean size of 150 $mm^3$, mice were then sorted into treatment groups (n=6) that received 7 daily injections of vehicle or Antp-AAC-11-LZ (363-399) peptide (2.4 mg/kg). Tumor volume was plotted as a function of time (mean±SEM).

Figure 9:
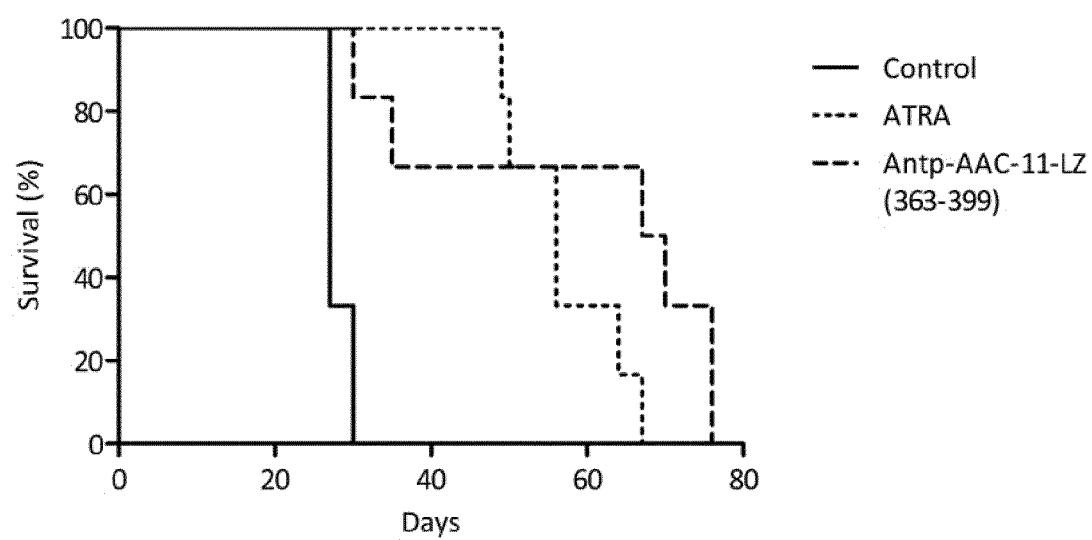

FIG. 9: Antp-AAC-11-LZ (363-399) peptide treatment of leukemic mice protects against disease progression. Mice were challenged with $10^4$ leukemic cells isolated from hMRP8-PML/RARα transgenic mice, allowed to engraft for 10 d, and were then injected intraperitonaly each day for 7 consecutive days with Antp-AAC-11-LZ (363-399) peptide (1.8 mg/kg) or vehicle (normal saline solution), or subcutaneously implanted with a 21-d release pellet containing 5 mg ATRA (n=6 for each treatment). Mice were monitored for survival.

FIG. 10: Antp-AAC-11-LZ (377-399) peptide inhibits cell migration and invasion. (A) U2OS cells were added to the upper well of modified Boyden chamber (transwell) plates in serum-free medium containing 0.4% BSA with a vehicle or with either 7.5 µM of the Antp-AAC-11-LZ (377-399) peptide or the AAC-11-LZ (377-399) peptide and subjected to a transwell migration assay as described under Materials and methods. The cells were allowed to migrate toward 10% FBS for 24 h. Triplicate wells were used for each of three independent experiments. The results are expressed relative to the migration of the untreated cells (=100%). Column: Mean of three experiments. Bar: s.e. P-value was determined by Student's t-test (*P<0.01). (B) U2OS cells were seeded in a Matrigel-coated Boyden chamber in serum-free medium containing 0.4% BSA with a vehicle or with either 7.5 □M of the Antp-AAC-11-LZ (377-399) peptide or the AAC-11-LZ (377-399) peptide and subjected to a transwell migration assay as described under Materials and methods. The cells were allowed to migrate toward 10% FBS for 48 h. Triplicate wells were used for each of three independent experiments. The results are expressed relative to the migration of the untreated cells (=100%). Column: Mean of three experiments. Bar: s.e. P-value was determined by Student's t-test (*P<0.01)

FIG. 11: (A) Effect of the Antp-AAC-11-LZ (377-399) peptide injection on body weight. Nude mice were injected intraperitoneally twice a week for 4 weeks with normal saline solution or the indicated doses of Antp-AAC-11-LZ (377-399) peptide (n=3-4 mice per group) and were monitored daily for body weight (mean±s.e.m). (B) Reduction of tumor growth in a mouse model of lung adenocarcinoma as a result of systemic administration of the Antp-AAC-11-LZ (377-399) peptide. A549 cells were subcutaneously implanted into female athymic nude mice. Once tumors reached a mean size of 100 mm$^3$, mice were then sorted into treatment groups (n=6) that received 7 daily injections of vehicle, AAC-11-LZ (377-399) peptide or Antp-AAC-11-LZ (377-399) peptide (5 mg/kg). Tumor volume was plotted as a function of time (mean±SEM).

EXAMPLE

Material & Methods

Cell Culture

Cells were cultivated in Dulbecco's Modified Eagle Medium (A549, H1299, MCF-7, Skov3, CT-26, 1205, B16, U2OS, WM-266-4, HaCat, NCTC and Human Skin Fibroblast cells), Minimum Essential Media (D3H2LN) or RPMI 1640 (Karpas_1106, DHL-5, Seax, HuT-78 cells) (Life Technologies), supplemented with 10% fetal bovine serum (FBS), 200 mg/ml penicillin and 100 mg/ml streptomycin sulfate.

Analysis of Cell Death

Cell death was evaluated upon staining with propidium iodide and flow cytometry analysis.

Viability of cells cultured in the 96-well culture plates was assessed by measuring mitochondrial dehydrogenase activity, using the colorimetric CellTiter 96® AQueous One Solution Cell Proliferation Assay (Promega), according to the manufacturer' instructions. In these assays, MTS [3-(4, 5-dimethylthiazol-2-yl)-5-(3-carboxymethoxyphenyl)-2-(4-sulfophenyl)-2H-tetrazolium, inner salt] is used in combination with the intermediate electron acceptor reagents phenazine ethyl sulfate (PES) which can penetrate viable cells, become reduced in the cytoplasm or at the cell surface and exit the cells where they can convert the MTS tetrazolium compound into a colored formazan product that is soluble in tissue culture medium. The number of proliferating (viable) cells is directly proportional to the level of formazan product created. The color can then be quantified using a simple colorimetric assay. The results are read on a multiwall scanning spectrophotometer (ELISA reader).

Detection of Lactate Dehydrogenase Activity in Culture Supernatants.

Cytoplasmic lactate dehydrogenase (LDH) release into the cell culture supernatant occurs upon damage of the plasma membrane, and it is therefore considered a typical hallmark of necrosis. Media was collected from 96-well plates into microcentrifuge tubes and briefly spun at 200 g to remove possible cell debris. LDH activity was measured using the CytoTox 96® assay (Promega) by the reduction of lactate to pyruvate in the presence of NAD$^+$. The resultant NADH reduces INT, a tetrazolium salt, to form a red formazan product that is detectable at 490 nm. The amount of color formed is proportional to the number of lysed cells. Visible wavelength absorbance data are collected using a standard 96-well plate reader. Results were normalized to maximal LDH release following treatment with 0.8% Triton X-100 as directed by the manufacturer.

Peptides Design and Synthesis

The inventors have designed peptides that encompass the leucine-zipper (LZ) domain of AAC-11 (residues 363-399). Furthermore, we have designed peptides that have the leucine residues (position 377, 384 and 391, AAC-11 numbering) mutated to glycine to determine if this will still be tumor cells lethal under conditions of serum deprivation. Peptides (>98% pure) were synthesized by Proteogenics Strasbourg-France. As compared to the AAC-11-LZ peptides described in our previous paper (Rigou et al., 2009), peptides used here were modified by N-terminal acetylation and C-terminal amidation. These chemical modifications were found to drastically enhance stability toward digestions by aminopeptidases and increase permeability of cells, therefore resulting in a marked increase of peptide efficiency (cytotoxic effect toward cancer cells). Peptides were diluted at a concentration of 1 mM in H2O and kept frozen at −70° C. The sequences of used peptides are listed in Table 1.

Immunocytochemistry

Coverslips were washed in PBS and cells fixed in 3% Paraformaldehyde for 7 minutes and finally washed two times 5 minutes in PBS with 50 mM of NH$_4$Cl. Cells were permeabilized with 0.5% Saponin for 10 minutes at 37° C. Blocking was carried out by washing two times 5 minutes in blocking buffer (PBS, 0.5% Saponin and 3% BSA). Primary and secondary antibody incubation were carried out at room temperature for 1 hour in blocking buffer and washes were performed using blocking buffer. AAC-11 was detected using anti-AAC-11 polyclonal antibody (ab65836, Abcam) in combination with Alexa fluor 647. Nuclei were counterstained with 4'-diamino-2-phenylindole (DAPI). Images were acquired by confocal microscopy on a Zeiss LSM 510 META confocal laser microscope (Zeiss, Oberkochen, Germany) with a Plan Apochromat 63×N.A.1.4 oil-immersion objective using the LSM510 software v4.0 (Zeiss).

Western Blotting

Cells were lysed in 50 mM Tris/HCl pH 7.6, 150 mM NaCl containing 1% NP-40, 10 µg·ml-l leupeptin and aprotinin and 0.1 mM PMSF and clarified by centrifugation at 15,000 g for 15 min. The proteins were resolved by SDS-PAGE and transferred to PVDF membrane (Biorad). Immunoblotting were performed using anti-AAC-11 antibody (ab65836, Abcam) and polyclonal anti-tubulin A5441 antibody (Sigma). The signal was detected using enhanced chemiluminescence detection reagent (Amersham).

Transwell Migration and Invasion Assays

Assays were performed using a modified Boyden chamber (Corning Costar, Rochester, N.Y., USA) containing a gelatin-coated polycarbonate membrane filter (6.5 mm diameter, 8 µm pore size). For invasion assays, the upper surface of the filter was coated with 20 µl or 50 µl Matrigel (BD Biosciences, San Jose, Calif., USA). The upper chamber contained cells in culture medium ($1.5 \times 10^5$/ml) with 1% FBS or 0.4% BSA, and the lower chamber contained culture medium with 10% FBS (chemoattractant). Cells were incubated for 12 h at 37° C. in 5% CO2 or 24 h for migration assays or for 48 h for invasion assays at 37° C. in 5% CO2. Cells that did not migrate or invade were scraped from the upper surface of the membrane with a cotton swab, and the remaining cells remaining on the bottom surface were counted in five randomly chosen fields under the optical microscope after staining with crystal violet.

Animals

All procedures complied with European or national regulations.

Lung Adenocarcinoma Model.

A549 cells ($1.25 \times 10^6$) were injected subcutaneously to six weeks old female nu/nu mice. Following transplantation (n=5-6 per model) tumor growth was assessed by measuring tumor size in two dimension using a Vernier caliper. Tumor volume was calculated using the formula [3.14×long axis× short axis×short axis]/6 (Kjonniksen et al., 1989). Treatment started after randomisation when tumor volumes had reached a size of approximately 100 mm³ and consisted of intraperitoneal injection of AAC-11-LZ (377-399) or Antp-AAC-11-LZ (377-399) peptides (5 mg/kg) or vehicle (normal saline solution) each day for 7 consecutive days. Mice were weighted and the tumor size was measured by a caliper and recorded daily. Twenty eight days after beginning of the treatment mice were sacrificed. The tumors, kidney, lungs, heart, liver, pancreas and spleen were taken and fixed. Paraffin-embedded sections were prepared and stained with hematoxylin and eosin for histological analysis.

Triple-Negative Breast Cancer Patient-Derived Primary Tumor Xenografts (PDX).

Breast cancer fragments were obtained from patients at the time of surgery, with informed written patient consent. After imaging-guided human tumor biopsies had been performed, fragments of 30 to 60 mm³ were subcutaneously grafted in 6-week-old NMRI-nude mice (Centre-Elevage-Janvier, France), under xylasin (10 mg/kg)/ketamin (100 mg/kg) anesthesia. Mice were maintained in specific pathogen-free animal housing (Institut Universitaire d'Hematologie) and received estrogen (17 mg/mL) diluted in drinking water. Xenografts were characterized and subsequently subcutaneously transplanted from mouse to mouse. Histology, biological profile and response to standard treatments of these xenografts showed close similarity to the original cancers (Marangoni et al., 2007; Varna et al., 2009). Two human triple-negative breast cancer (HBC) xenografts models were used in our experiments (PDX01 and PDX02). PDX01 showed a partial response to chemotherapy and PDX02 was nonresponder (Bousquet G. et al., manuscript in preparation). Following transplantation (n=6 per model) tumor growth was assessed by measuring tumor size in two dimension using a Vernier caliper. Tumor volume was calculated using the formula [3.14×long axis×short axis×short axis]/6 (Kjonniksen et al., 1989). Treatment started after randomisation when tumor volumes had reached a size of approximately 150 mm³ and consisted of intraperitoneal injection of Antp-AAC-11-LZ (363-399) peptide (2.4 mg/kg) or vehicle (normal saline solution) each day for 7 consecutive days. Mice were weighted and the tumor size was measured by a caliper and recorded daily. Fourteen days after beginning of the treatment mice were sacrificed. The tumors, kidney, lungs, heart, liver, pancreas and spleen were taken and fixed. Paraffin-embedded sections were prepared and stained with hematoxylin and eosin for histological analysis.

Acute Promyelocytic Leukemia (APL) Model.

We use an established in vivo APL model based on syngenic grafts of leukemic blasts from hMRP8-PML/RARα transgenic mice, as described by Brown et al. (Brown et al., 1997). This model mimics human APL, both in its biological characteristics and its response to conventional therapeutic drugs such as all-trans retinoic acid (ATRA) and 100% of the mice die of the disease (Brown et al., 1997; Kogan et al., 2000; Lallemand-Breitenbach et al., 1999). 104 leukemic cells isolated from bone marrow, spleen, or lymph nodes of leukemic hMRP8-PML/RARα transgenic mice (Brown et al., 1997) were injected into the tail vein of 6-7 week old syngeneic FVB/N mice. Establishment of leukemia was assessed by the appearance of high leukocyte and low platelet counts at around day 8 (Brown et al., 1997). Ten days after transplantation, mice implanted with leukemic cells were randomly assigned to either type of treatment (n=6). Antp-AAC-11-LZ (363-399) peptide (1.8 mg/kg) or vehicle (normal saline solution) was injected intraperitonaly each day for 7 consecutive days. Retinoic acid was administrated by subcutaneous implantation of a 21-d release pellet containing 5 mg ATRA (Innovative Research of America). Mice were then monitored for survival.

Statistical Analysis

Data are represented as a mean and SD. Statistical differences between two groups were evaluated using the independent t-test. One-way analysis of variance was used for the comparisons between three or more groups. A P-value of <0.05 was considered statistically significant.

Results

AAC-11 Leucine-Zipper Peptide Design

The inventors designed cell-permeable peptides (CPPs) spanning the LZ of AAC-11 as cytotoxic agents of cancer cells. The wild-type peptide (AAC-11-LZ (363-399), Table 1) consisted of the region from residues 363-399 of the AAC-11 fused at the N-terminus or at the C-terminus to an internalization sequence derived either from the homeodomain of *Drosophila* Antennapedia/Penetratin (Antp) protein (amino acids 43-58) (Antp-AAC-11-LZ (363-399) and Cter-Antp-AAC-11-LZ (363-399) peptides, respectively)) or the Transactivator of Transcription (TAT) cell penetrating sequences (TAT-AAC-11-LZ (363-399) peptide). The mutant peptide (Antp-AAC-11-LZ (363-399) L/G) was identical except that leucines 377, 384 and 391 in the LZ were mutated to glycines.

Figure 1B:
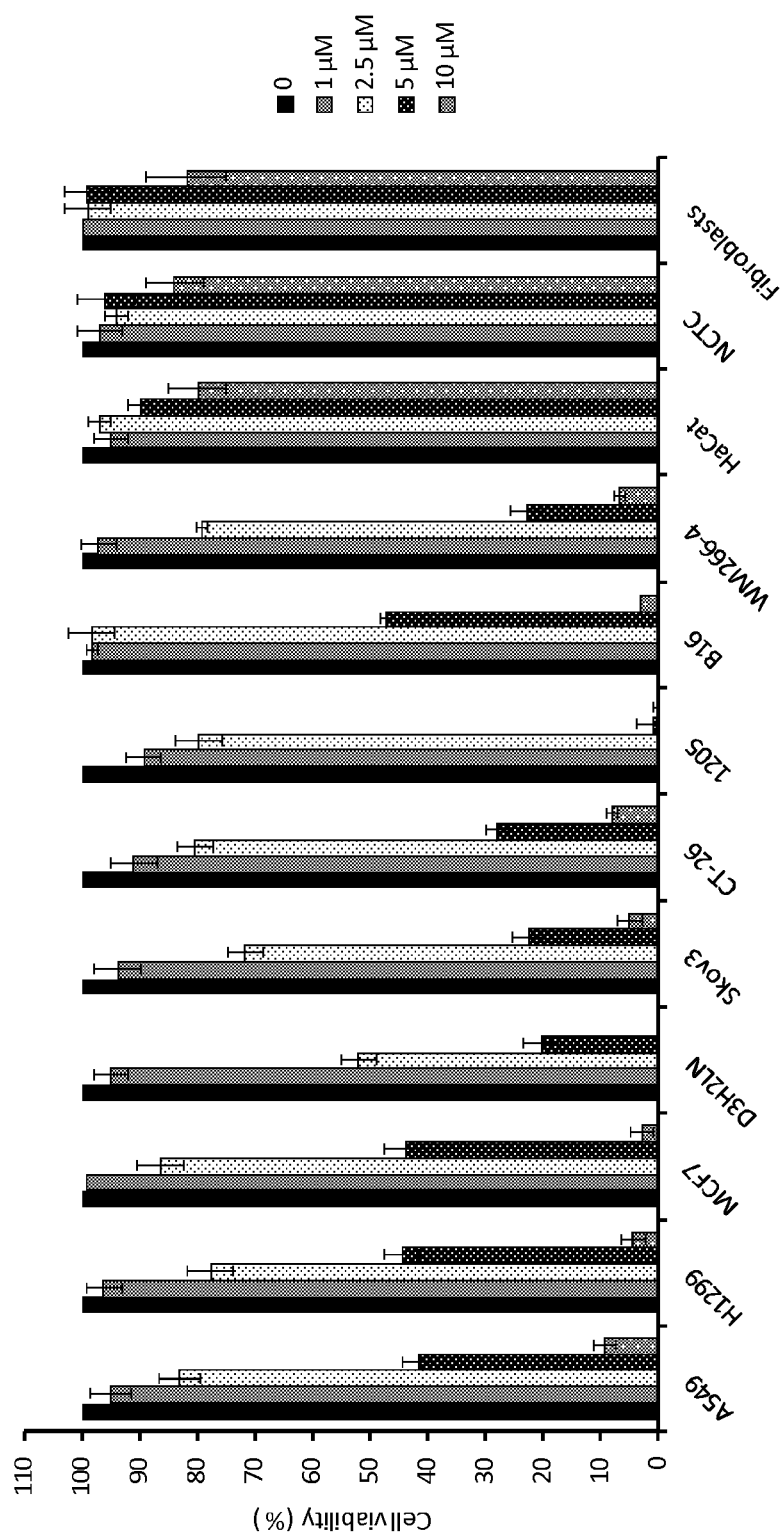
Figure 1C:
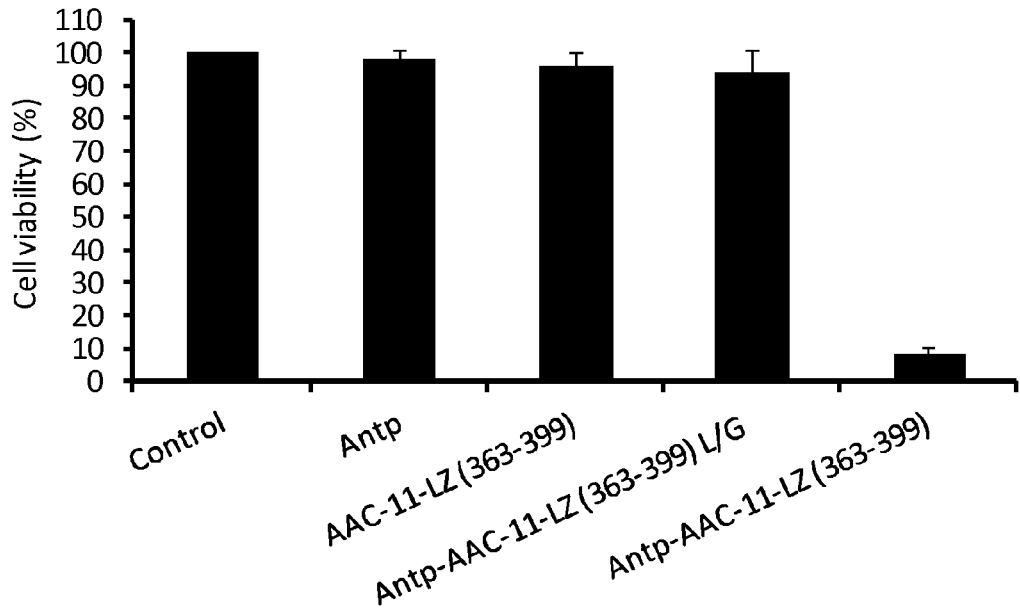

Cytotoxic Effects of Cell-Permeable Antp-AAC-11-LZ (363-399) Peptide on Various Cancer Cells The inventors evaluated the capacity of the Antp-AAC-11-LZ (363-399) peptide to induce cell death a panel of hematologic and solid tumor cell lines, both P53 positive and P53 negative, derived from different tissues of origin, under low serum conditions (0.5-5%). The inventors first assessed the sensitivity of the hematologic cancer cell lines (B-cell non-Hodgkin's lymphoma cell lines Karpas 1106 and SU-DHL-5 and T-acute lymphoblastic leukemia cell lines SeAx and HUT-78) towards increasing concentrations of the Antp-AAC-11-LZ (363-399) peptide. As shown in (FIG. 1A), drastic loss of cellular viability was observed for all cell lines upon exposure to the Antp-AAC-11 LZ (363-399) peptide, in a dose-related manner. The inventors then studied the cytotoxic effect of the Antp-AAC-11-LZ (363-399) peptide on an array of solid tumor cell lines as well as normal cells (HaCat, NCTC and human primary fibroblasts). As shown in FIG. 1B, a marked cell viability loss of the cancer cell lines was observed towards increasing concentrations of the Antp-AAC-11-LZ (363-399) peptide. Moreover, this toxicity seemed to be independent of the P53 status of the cancerous cell lines, as both P53 positive cells (the lung adenocarcinoma A549 cells for instance) and P53 null cells (the lung adenocarcinoma H1299 cells for instance) were used in this assay. Interestingly, the Antp-AAC-11-LZ (363-399) peptide elicited much reduced toxicity in the normal cells tested (HaCat, NCTC and primary fibroblast) (FIG. 1B), indicating that the Antp-AAC-11 LZ (363-399) peptide exhibits specific toxicity to cancer cells. In contrast to what observed with the wild type peptide, neither the Penetratin peptide alone, the AAC-11-LZ (363-399) peptide without the Penetratin linkage nor the mutant peptide Antp-AAC-11-LZ (363-399) L/G did induce cell death of A549 cells (FIG. 1C). This indicates that the cytotoxic effect of the Antp-AAC-11-LZ (363-399) peptide is specific to the amino acid sequence and is not a nonspecific effect of the peptide or the leader sequence. Of note, the osmolarities of the different media containing or not 10% serum were found to be similar (around 280 mOsmol for serum containing media vs 270 mOsmol for serum-free media, data not shown), thus excluding any role for osmolaric effect for the observed Antp-AAC-11 LZ (363-399) peptide cytotoxicity. These data suggest that the Antp-AAC-11-LZ (363-399) peptide is cancer cells lethal at micromolar concentrations in condition of growth factor deprivation.

Figure 2A:
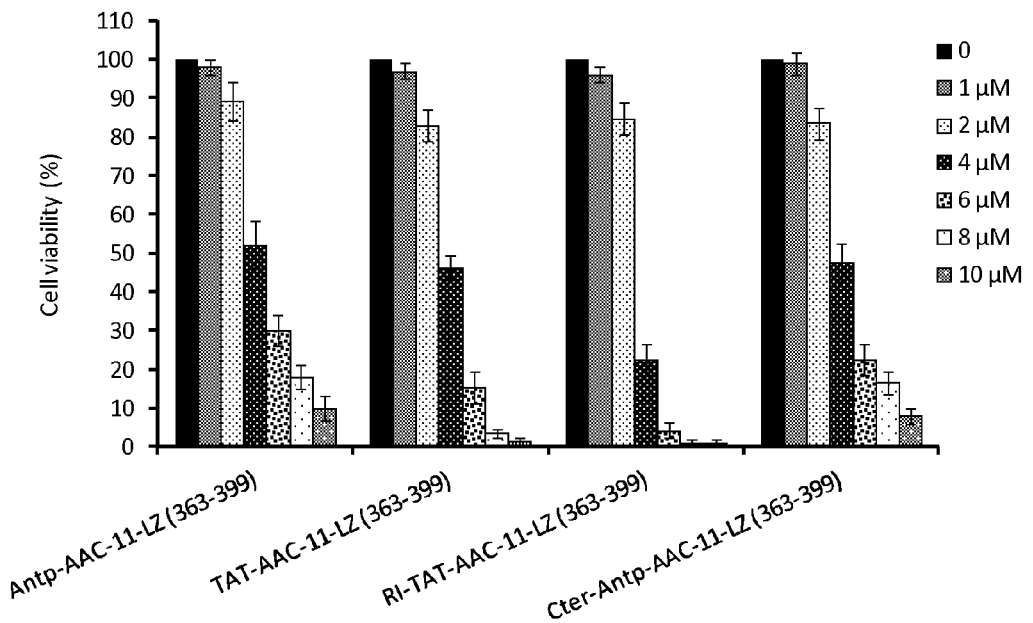
Figure 2B:
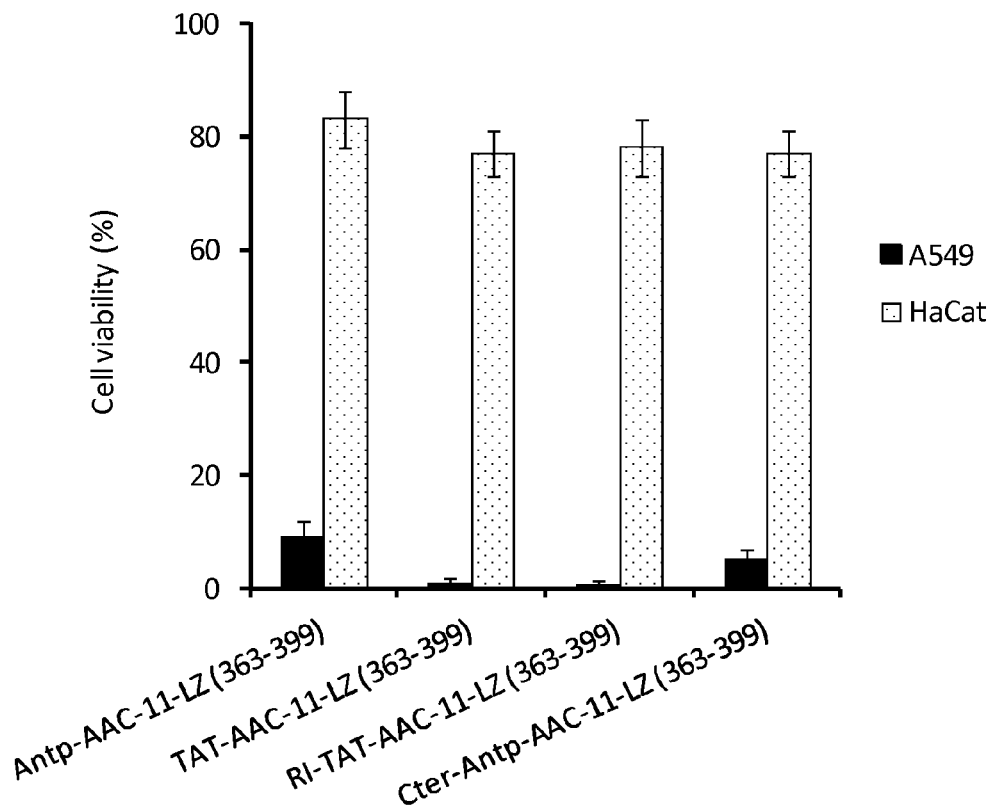

The inventors next investigated the effect of the internalization sequence upon cancer cell toxicity by conjugating the AAC-11 (363-399) domain to the Transactivator of transcription (TAT) cell penetrating sequence, a basic peptide sequences derived from the HIV TAT protein (amino acids 49-57). TAT conjugation has been extensively used for the in vitro and in vivo delivery of biological active peptides and proteins (Heitz et al., 2009). Uptake of the resulting TAT-AAC-11-LZ (363-399) peptide was comparable to the Antp-AAC-11-LZ (363-399) peptide (data not shown). We then assayed the cytotoxicity of the TAT-AAC-11-LZ (363-399) peptide to both normal and tumor cells. Dose-response analyses indicate that the TAT-AAC-11-LZ (363-399) peptide was at least as effective as compared to the Antp-AAC-11-LZ (363-399) peptide for decreasing A549 cancer cells viability when cultured in low-serum conditions (FIG. 2A). Similar results were obtained when the TAT-AAC-11-LZ (363-399) peptide was used in the solid tumor cell lines H1299, MCF7, U2OS, D3H2LN, Skov3, CT-26, 1205, B16, WM266-4 and the hematologic tumor cell lines Karpas_1106, DHL-5, Seax and HuT-78 (data not shown). Interestingly, the nonmalignant cells were largely more resistant to TAT-AAC-11-LZ (363-399) peptide (FIG. 2B). These results indicate that the TAT-AAC-11-LZ (363-399) peptide is preferentially toxic to tumor cells, as observed with the Antp-AAC-11-LZ (363-399) peptide. Finally, attaching the Antp sequence on the C-terminal as opposed to the N-terminal had no influence on the cytotoxic properties of the AAC-11 (363-399) domain as the resulting Cter-Antp-AAC-11-LZ (363-399) peptide displayed similar cytotoxicity as the Antp-AAC-11-LZ (363-399) peptide towards cancerous cells, but not normal cells (FIGS. 2A and 2B). Uptake of the Cter-Antp-AAC-11-LZ (363-399) peptide was comparable to the Antp-AAC-11-LZ (363-399) peptide (data not shown). Therefore, AAC-11 (363-399) domain-containing chimeric peptides that use different CPPs as their leader peptides display a similar degree of toxicity in tumor cell, while sparing nonmalignant cells.

Despite their ability to bind proteins with high affinity and unsurpassed specificity, the susceptibility of peptides to proteolytic degradation in vivo often remains problematic for their use as therapeutics. One way to render a peptide resistant to proteases involves the use of D-amino acids in lieu of the natural L-form. Retro-inverso peptides are composed of D-aminoacids assembled in the reverse order from that of the parental L-sequence. This double inversion of peptide structure is postulated to preserve the overall surface topology of the parent L-peptide (Chorev and Goodman, 1995), thus leading to high degree of topochemical equivalence, and at the same time provides high stability to proteolysis (Fischer, 2003). Because of their greater stability, retro-inverso peptides often display increase potency. We therefore synthesized a retro-inverso version of the TAT-AAC-11-LZ (363-399) peptide and compared the resulting RI-TAT-AAC-11-LZ (363-399) peptide and the parental L-isomer for their cytotoxic properties. Interestingly, dose-responses analyses indicated that the RI-TAT-AAC-11-LZ (363-399) peptide was more effective than the TAT-AAC-11-LZ (363-399) peptide in decreasing A549 cancer cells viability under low-serum conditions (FIG. 2A), whereas very little cytotoxicity occurred in the nonmalignant cells tested (FIG. 2B). Similar results were obtained when the RI-TAT-AAC-11-LZ (363-399) peptide was used in the solid tumor cell lines H1299, MCF7, U2OS, D3H2LN, Skov3, CT-26, 1205, B16, WM266-4 and the hematologic tumor cell lines Karpas_1106, DHL-5, Seax and HuT-78 (not shown). Therefore, our results show that the RI-TAT-AAC-11-LZ (363-399) peptide retains full functionality and, like the parental L-isomer, its cytotoxic effect is selective for the transformed cells.

Cell death can occur by either necrosis or apoptosis. To determine whether the Antp-AAC-11-LZ (363-399) peptide induces caspase-dependent apoptosis in low serum conditions, we evaluated cellular viability of A549 cells treated with the Antp-Antp-AAC-11-LZ (363-399) peptide in the presence or absence of the pan-caspase inhibitor Z-VAD-FMK. As seen in FIG. 3, Z-VAD-FMK did not rescue, but somehow increased, the Antp-AAC-11-LZ (363-399) peptide induced-cytotoxicity, suggesting that the observed cell death is not dependent of caspases, whereas as a control, Z-VAD-FMK was able to efficiently inhibit cisplatin-induced cell death. The same results were observed with the TAT-AAC-11-LZ (363-399) peptide and the RI-TAT-AAC-11-LZ (363-399) peptide (data not shown).

To determine if protein synthesis was involved in the cytotoxic effect of the Antp-AAC-11-LZ (363-399) peptide, we evaluated cellular viability of A549 cells treated with various concentrations of the Antp-AAC-11-LZ (363-399) peptide in the presence or absence of 10 $\mu$M of the protein synthesis inhibitor cycloheximide (CHx). Cycloheximide had no influence on the Antp-AAC-11-LZ (363-399) peptide induced-cytotoxicity compared to the peptide alone (data not shown), suggesting that the AAC-11-LZ (363-399) peptide does not depend on de novo protein synthesis for it cytotoxic action. The same results were observed with the TAT-AAC-11-LZ (363-399) peptide and the RI-TAT-AAC-11-LZ (363-399) peptide (data not shown).

Figure 4A:
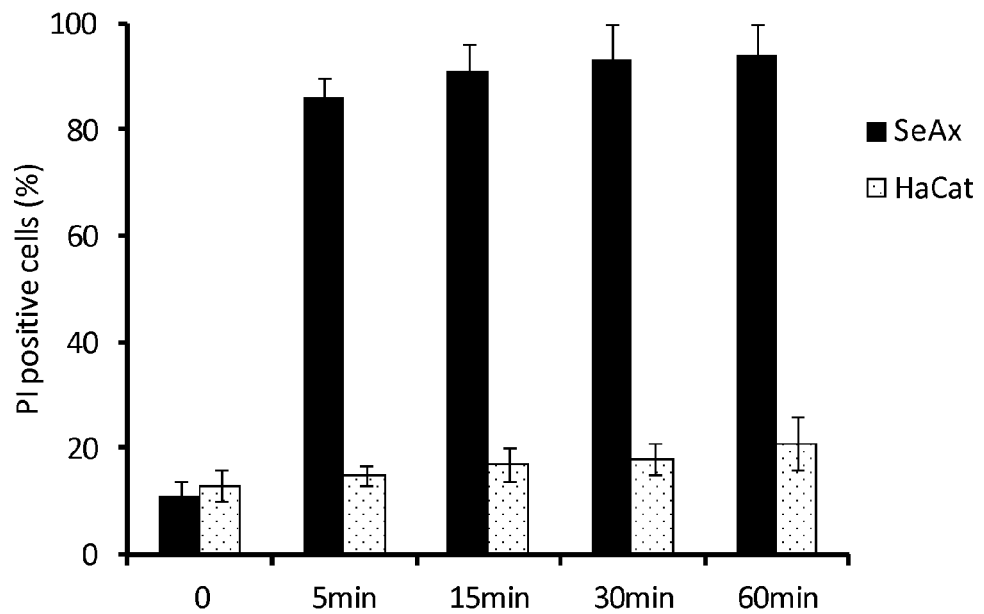

Loss of plasma membrane integrity, as demonstrated by the ability of a membrane-impermeable propidium iodide (PI) to label the nucleus, represents a straightforward approach to demonstrate necrosis. We therefore evaluated necrotic cell death of SeAx cells treated with the Antp-AAC-11-LZ (363-399) peptide by PI uptake assay following different time exposures. Under these experimental conditions, PI is excluded by cells with intact membranes, and PI positivity can thus be taken as an index of necrosis. As shown in FIG. 4A, SeAx cells displayed an increasing loss of plasma membrane integrity extremely rapidly after exposure to 4 µM of the Antp-AAC-11-LZ (363-399) peptide. Indeed, 90% of cells were PI positive after only 5 minutes of 4 µM Antp-AAC-11-LZ (363-399) peptide treatment, indicating loss of membrane integrity and leakage. This value remained unchanged up to 60 minutes. Similar results were obtained with DHL-5, HuT-78 and A549 cells (data not shown). Interestingly, Antp-AAC-11-LZ (363-399) peptide treatment of the nonmalignant cells HaCat resulted in much decreased loss of cell membrane integrity (FIG. 4A). Similar results were obtained with the TAT-AAC-11-LZ (363-399) peptide and the RI-TAT-AAC-11-LZ (363-399) peptide (data not shown). Therefore, these results suggest that very short (minute) exposure of micromolar concentrations of the Antp-AAC-11-LZ (363-399) peptide induces loss of plasma membrane integrity in cancer cells, but not in normal cells, when cultured in low serum conditions, as typically occurs from necrotic cell death.

Figure 4B:
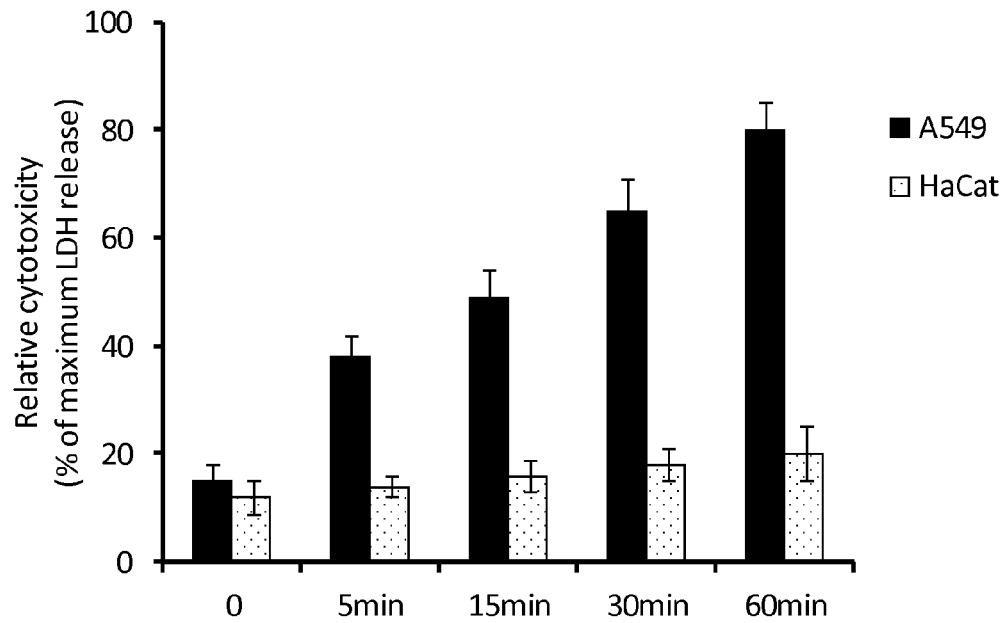

Necrosis was further assessed based on lactate dehydrogenase (LDH) activity release in the culture medium. LDH is a soluble cytosolic enzyme that is released into the culture medium following loss of membrane integrity resulting from necrosis. LDH activity in the cellular medium, therefore, can be used as an indicator of cell membrane integrity and serves as a general indicative of cellular necrosis. As shown in FIG. 4B, Antp-AAC-11-LZ (363-399) peptide exposure resulted in a drastic increase in LDH release into A549 cell supernatants, indicating membrane damage and necrotic cell death, whereas untreated cells or nonmalignant HaCat cells showed little LDH release. This effect was extremely rapid, as after only 5 minute of 10 µM Antp-AAC-11-LZ (363-399) peptide treatment, high (nearly 40%) levels of LDH release was detected in A549 cell supernatants. Compared to maximum LDH release following treatment with 0.8% Triton X-100, 80% of LDH release was observed following 1 hour exposure to 10 µM of Antp-AAC-11-LZ (363-399) peptide. Similar results were obtained with the TAT-AAC-11-LZ (363-399) peptide and the RI-TAT-AAC-11-LZ (363-399) peptide (data not shown). Combined, these data indicate that the Antp-AAC-11-LZ (363-399) peptide induces extremely fast necrosis, via membranolysis, of cancerous cells.

To better understand the function of Antp-AAC-11-LZ (363-399) peptide and to decipher the sequence determinants for its cytotoxic phenotype, we carried out sequence analyses of the peptide. We generated a series of N-terminal and/or C-terminal truncated variants fused to a N-terminal Penetratin to determine the minimal sequence required for the Antp-AAC-11-LZ (363-399) peptide cytotoxicity toward cancer cells (see Table 1). The effect of these variants on cell death was measured in A549 cells using an MTT assay. This approach should allow us to determine whether the Antp-AAC-11-LZ (363-399) sequence constitutes the lower size limit or whether shorter peptides can exhibit cancer cells death properties.

Figure 5A:
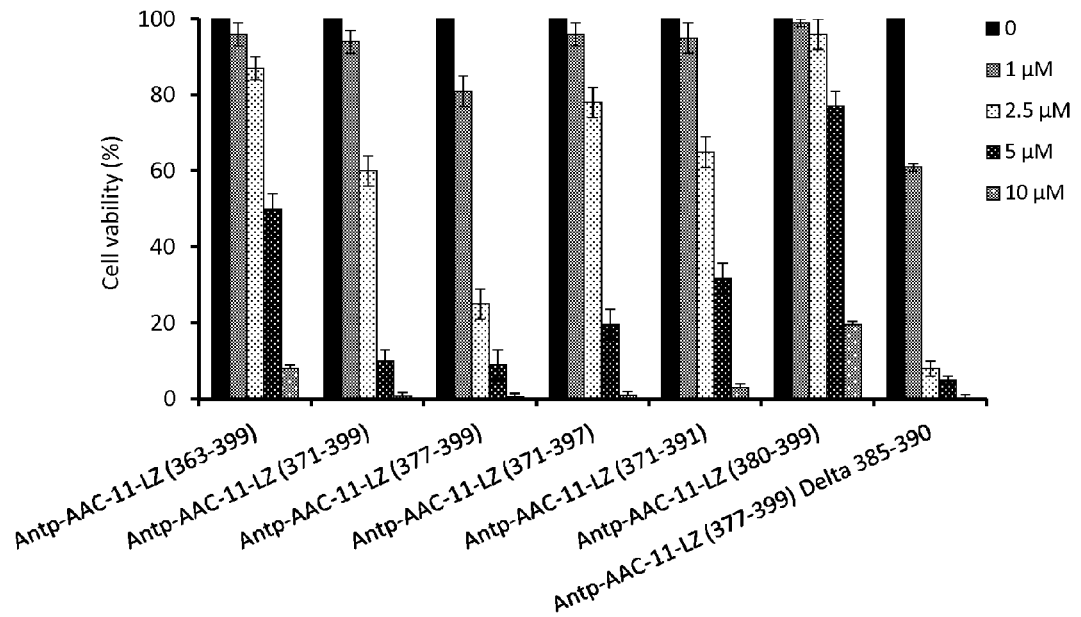

Surprisingly, as observed in FIG. 5A, dose response analyses indicated that truncation of the N-terminal amino acids 1-7 (AAC-11 domain sequence numbering) of the Antp-AAC-11-LZ (363-399) peptide resulted in markedly increased cytotoxicity potency compared to the parent peptide when cells were cultured in low serum conditions. Indeed, when used at 2 µM, the resulting Antp-AAC-11-LZ (371-399) and Antp-AAC-11-LZ (377-399) peptides reduced cellular viability to 33.2% and 5% of control, respectively, as compared to 97% of control with the parent peptide.

Further deletion of the last two (Antp-AAC-11-LZ (371-397) peptide) or eight (Antp-AAC-11-LZ (371-391) peptide) C-terminal residues resulted in reduced cytotoxicity compared with the Antp-AAC-11-LZ (371-399) peptide but still both the Antp-AAC-11-LZ (371-397) or Antp-AAC-11-LZ (371-391) peptides variants elicited a significantly higher cell death compared with the Antp-AAC-11-LZ (363-399) parent peptide (FIG. 5A).

Figure 5B:
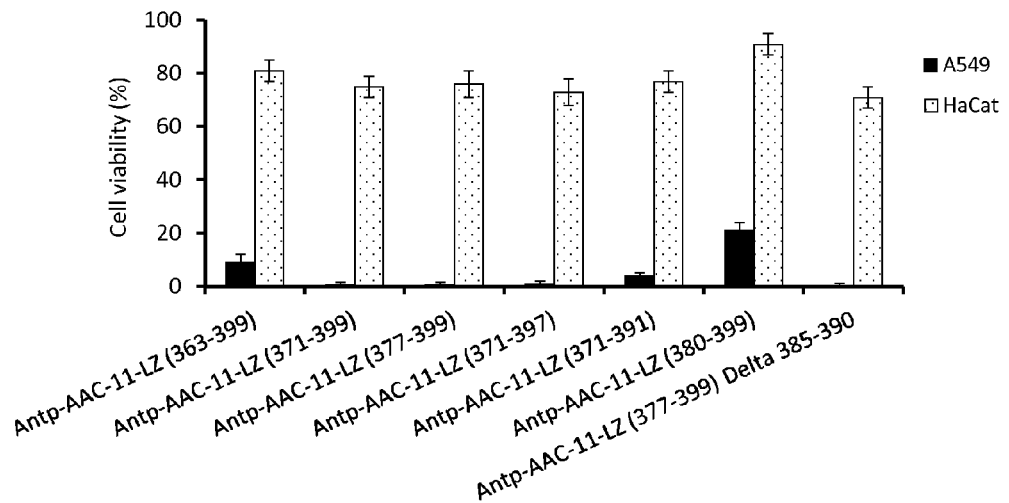

Very interestingly, deletion of a central domain of 5 residues of the Antp-AAC-11-LZ (377-399) peptide resulted in a form with the highest activity in inducing cancer cells death. Indeed, when used at 2 µM, the resulting Antp-AAC-11-LZ (377-399 4385-390) reduced cellular viability to 3% of control, respectively, as compared to 97% of control with the parent peptide. This indicates that residues 377-384 are required for cancer cell toxicity. To further narrow down the active sequence within the Antp-AAC-11-LZ (363-399) peptide, N-terminal truncations were assessed. Deletion of the first seventeen residues of the parent Antp-AAC-11-LZ (363-399) peptide resulted in a concomitant reduction of activity as the resulting Antp-AAC-11-LZ (380-399) peptide induced substantial but weaker cell death than the Antp-AAC-11-LZ (363-399) peptide (FIG. 5A). Similar results were obtained when the truncated peptides were used in the solid tumor cell lines H1299, MCF7, U2OS, D3H2LN, Skov3, CT-26, 1205, B16, WM266-4 and the hematologic tumor cell lines Karpas_1106, DHL-5, Seax and HuT-78 (not shown). Finally, compared to malignant cells, those peptides produced much reduced cytotoxicity in the nonmalignant cells HaCat (FIG. 5B). Combined, these results show that the truncated AAC-11-LZ peptides, like the parental peptide counterpart, induce preferential cancer cell death at micromolar concentrations and suggest that the residues 377-391 (AAC-11 specific sequence numbering) of the AAC-11-LZ (363-399) peptide are required for its toxicity and the residues 380-384 (AAC-11 specific sequence numbering) of the AAC-11-LZ (363-399) peptide constitute the minimal sequence for its toxicity toward cancer cells.

Figure 6A:
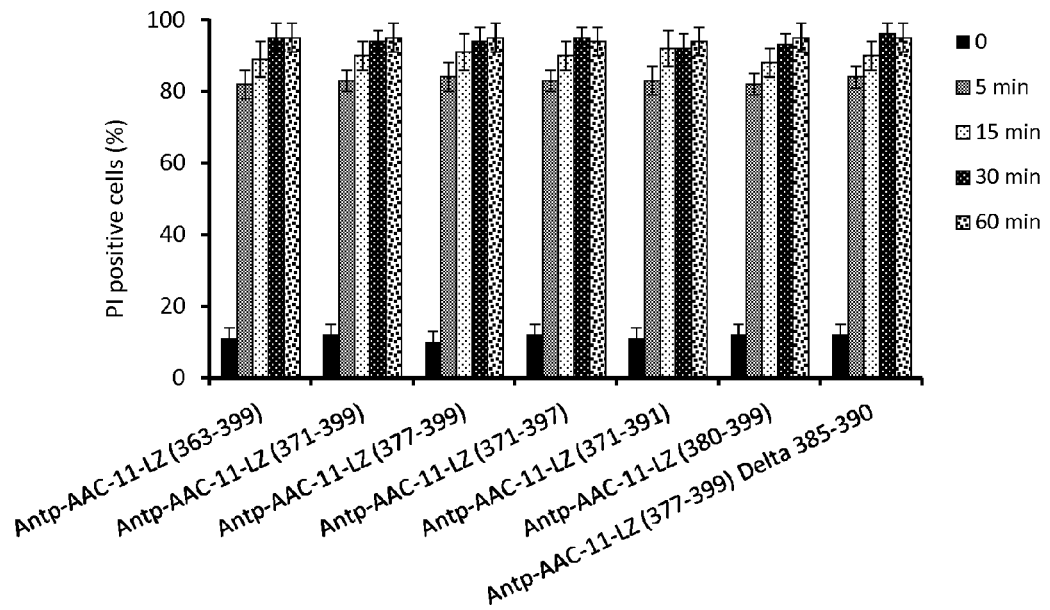
Figure 6B:
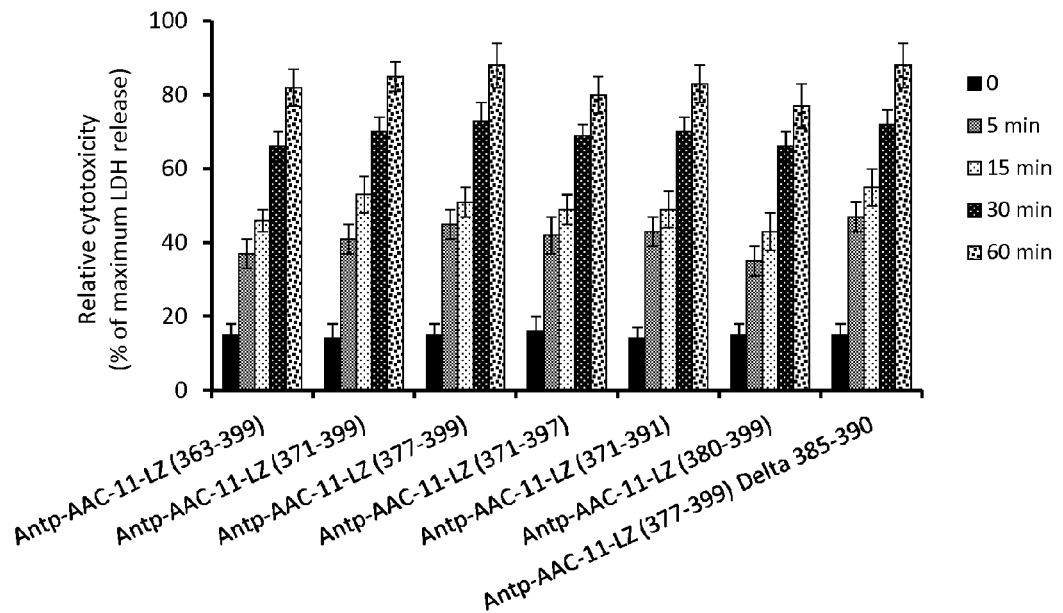

The inventors next examined whether the truncated AAC-11 peptides mediated-cytotoxicity was related to loss of cell membrane integrity, hence necrosis. PI exclusion analysis indicated that treatment of SeAx cells with 4 µM of the truncated peptides induced rapid plasma membrane permeability (FIG. 6A). Indeed, after 5 minutes treatment nearly 90% of the cells were PI positive when exposed to all the tested peptides. Moreover, time course analyses indicate that A549 cells treated with the truncated peptides showed massive LDH release (FIG. 6A). Once again this effect was extremely rapid as after only 5 minutes treatment, the peptides exhibited 30-50% LDH release (FIG. 6B). Combined, these data indicate that the truncated peptides induce cancer cell membranolysis, resulting in necrotic cell death and that the 377-391, particularly 380-384 fragment constitute the active motif of the full length Antp-AAC-11-LZ (363-399) peptide.

Figure 7A:
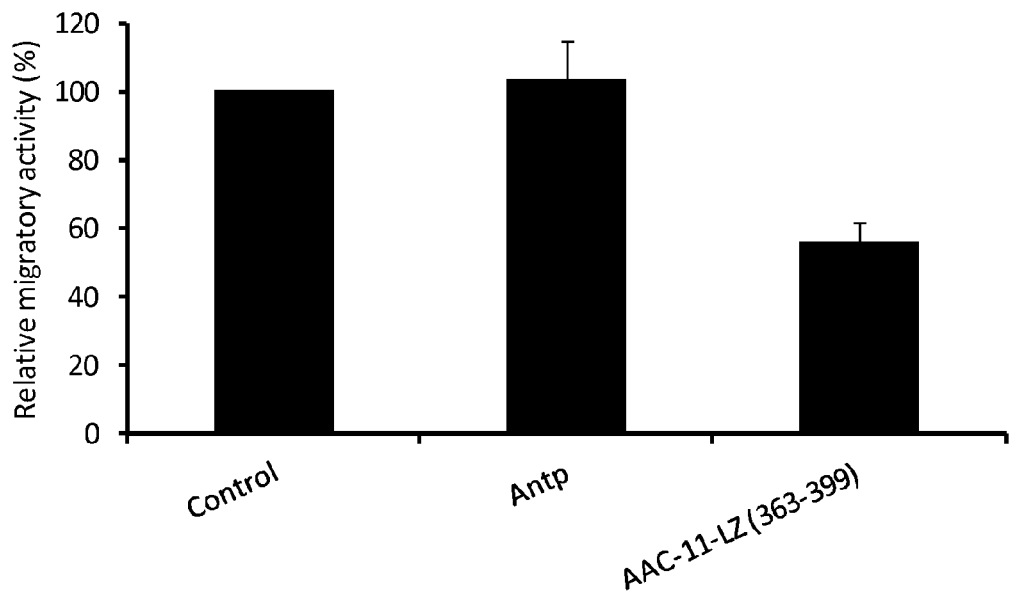
Figure 7B:
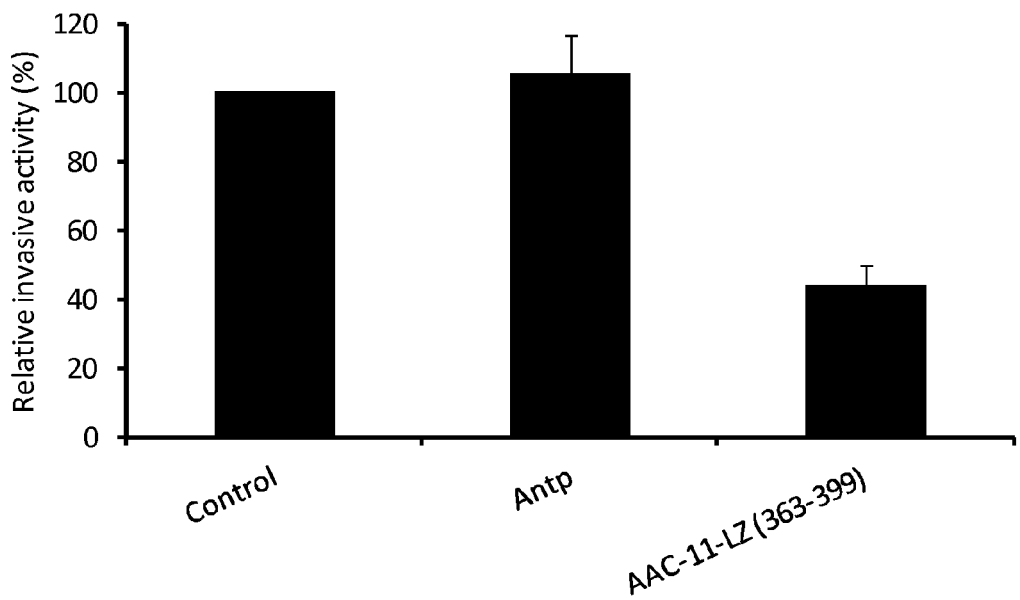

The Antp-AAC-11-LZ (363-399) Peptide Impairs Cancer Cells Migration and Invasion A hallmark of tumor cells is the ability to acquire an invasive phenotype and metastasize from the primary tumor and blocking invasion is a prime strategy to inhibit the initial steps of the metastatic dissemination. Although the molecular pathways controlling metastasis are now relatively well understood, there are no tools yet to effectively inhibit the critical steps of the metastasis cascade and, eventually, metastasis formation. Earlier reports have indicated that AAC-11 can control cell migration, as AAC-11 overexpression was found to increase cervical cancer cell increased cervical cancer cell colonization (Kim et al., 2000). We therefore evaluated the impact of the Antp-AAC-11-LZ (363-399) peptide on migration of the highly invasive, MDA-MB-231 breast cancer cell line-derived D3H2LN cells using a using transwell Boyden chamber migration assay. As shown in FIG. 7A, Antp-AAC-11-LZ (363-399) peptide treatment substantially decreased D3H2LN cells migration, whereas the Antp-only peptide didn't show any effect. Similar results were observed with the TAT-AAC-11-LZ (363-399) peptide (not showed). Of note, neither the Antp-AAC-11-LZ (363-399) or TAT-AAC-11-LZ (363-399) peptides impaired proliferation of the D3H2LN cells at the used concentrations, thus ruling out the possibility that impaired migration was a consequence of decreased proliferation (not showed). We next evaluated whether the Antp-AAC-11-LZ (363-399) peptide could hamper cell invasion. As shown in FIG. 7B, in an "invasion" assay, in which cells migrated though serial barriers consisting of a Matrigel layer and the porous filter, the Antp-AAC-11-LZ (363-399) peptide prevented invasion of the D3H2LN cells, whereas the Antp-only peptide didn't show any effect.

Figure 8A:
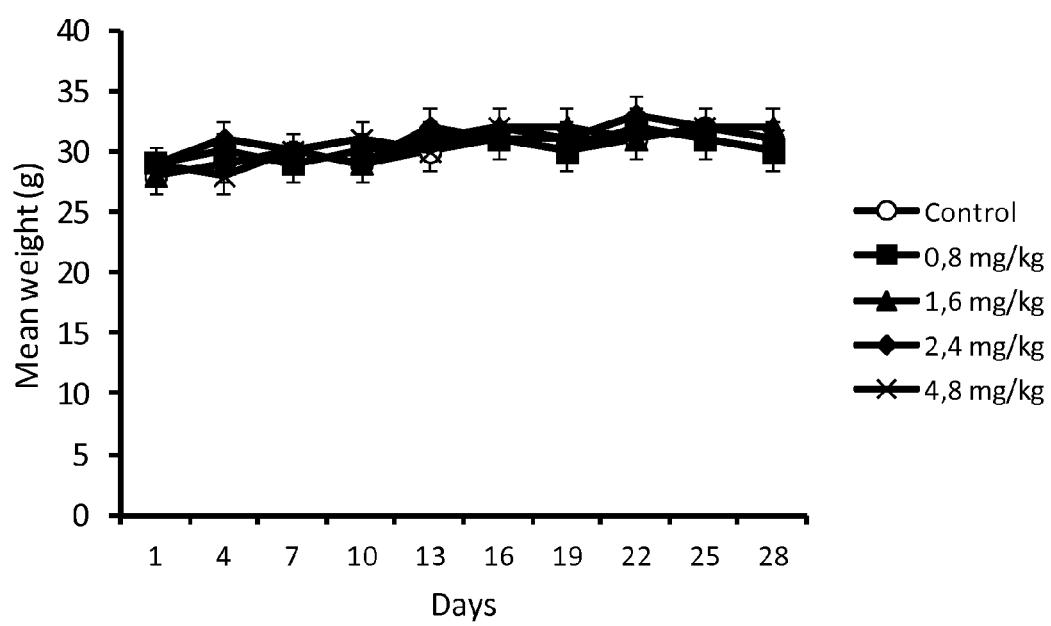

Systemic Delivery of the Antp-AAC-11-LZ (363-399) Peptide Inhibits Tumor Growth in Triple-Negative Breast Tumor Patient-Derived Xenograft (PDX) Mouse Models The inventors next investigated the effect of the AAC-11-LZ (363-399) peptide on distant solid tumor growth by using PDX triple-negative breast tumor mouse models. Triple-negative breast tumors were chosen as models for our in vivo xenograft studies as there is a clinical need to develop new therapies because they are not candidates for targeted therapy. We first evaluated the toxicity of the Antp-AAC-11-LZ (363-399) peptide in nude mice that were injected intraperitoneally twice per week for 4 weeks with the Antp-AAC-11-LZ (363-399) peptide or normal saline solution (dose range: 0.8-4.8 mg peptide/kg body weight; n=3-4 mice per group). No mice died during the experiment and there was no significant difference between the different groups in body weight (FIG. 8A). At the end of the experiment, no obvious toxicity was observed to the kidney, lungs, heart, liver, pancreas and spleen of mice injected with the peptide (data not shown).

Figure 8B:
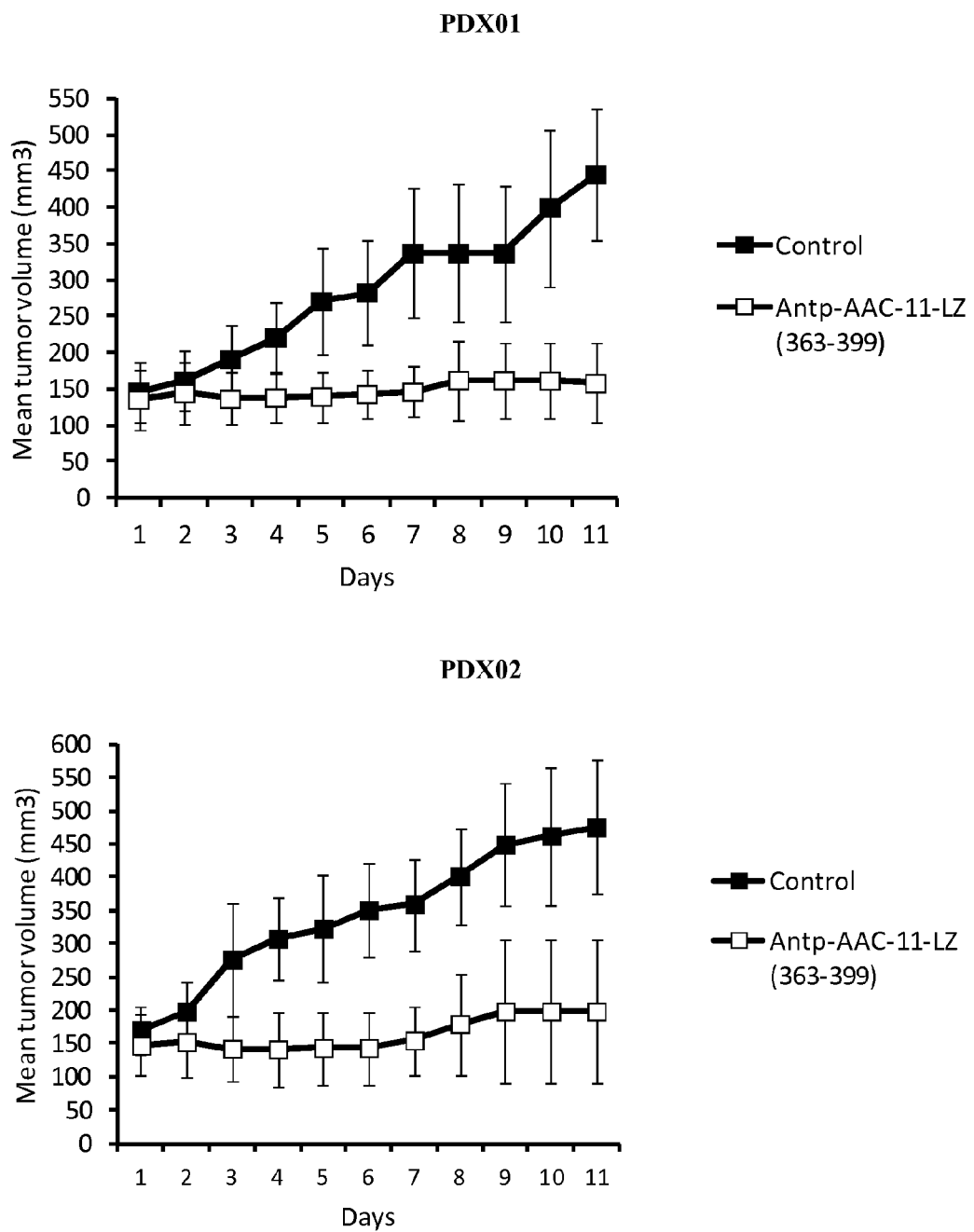

The inventors then evaluated the ability of the Antp-AAC-11-LZ (363-399) peptide to inhibit tumor growth using two nude mice groups bearing subcutaneous triple-negative breast tumor xenografts derived from two different patients' biopsies (PDX01 and PDX02). Response to standard treatments of these xenografts showed close similarity to the original cancers, PDX01 being a low responder and PDX02 a nonresponder (Bousquet G. et al., manuscript in preparation). As shown in FIG. 8B, mice treated with the Antp-AAC-11-LZ (363-399) peptide developed significantly smaller tumors than mice treated with vehicle, for both groups. Indeed, tumors in mice receiving the AAC-11 LZ (363-399) peptide reached a final mean volume less than 35% (PDX01) or less than 50% (PDX02) that of tumors in the control-treated mice (p=0.01). These data demonstrate that the Antp-AAC-11-LZ (363-399) peptide can inhibit by itself the growth of already formed and aggressively proliferating tumors.

Antp-AAC-11-LZ (363-399) Peptide Treatment of Acute Promyelocytic Leukemia

To broaden these results, the inventors tested the efficacy of the Antp-AAC-11-LZ (363-399) peptide in a mouse model of acute promyelocytic leukemia (APL). This model, based on syngenic grafts of leukemic blasts from PML/RARα transgenic mice, mimics human APL, both in its biological characteristics and its response to conventional therapeutic drugs such as all-trans retinoic acid (ATRA) (Brown et al., 1997; Kogan et al., 2000; Lallemand-Breitenbach et al., 1999). Control mice succumbed to tumor burden within a narrow time range (mean survival time of 27 d) (FIG. 9). As expected, ATRA treated mice had significantly extended survival compared with the control group (mean survival time of 56 d). Interestingly, Antp-AAC-11-LZ (363-399) peptide treatment resulted in survival that was superior to that obtained with ATRA (mean survival time of 68.5 d). Four of 6 mice injected with the Antp-AAC-11-LZ (363-399) peptide survived up to 67 d and 2 mice of that group survived up to 76 d, whereas only one mouse of the ATRA group lived up to 67 d. Enlargement of organs and tissue section examination confirmed that the cause of death was APL (Lallemand-Breitenbach et al., 1999) for all groups. These observations demonstrate that the Antp-AAC-11-LZ (363-399) peptide possesses strong antileukemic effect, resulting in significantly increased lifespan.

Figure 10A:
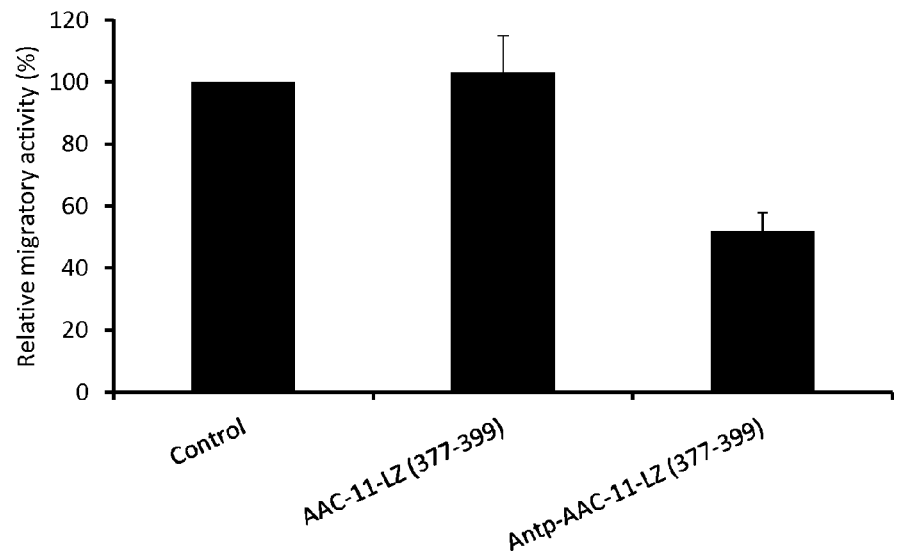
Figure 10B:
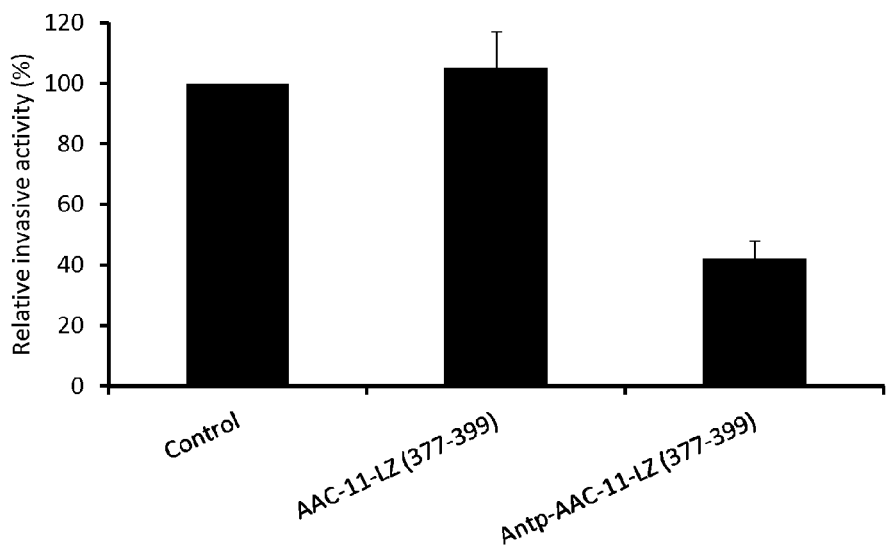

The Antp-AAC-11-LZ (377-399) Peptide Impairs Cancer Cells Migration and Invasion A hallmark of tumor cells is the ability to acquire an invasive phenotype and metastasize from the primary tumor and blocking invasion is a prime strategy to inhibit the initial steps of the metastatic dissemination. Although the molecular pathways controlling metastasis are now relatively well understood, there are no tools yet to effectively inhibit the critical steps of the metastasis cascade and, eventually, metastasis formation. Earlier reports have indicated that AAC-11 can control cell migration, as AAC-11 overexpression was found to increase cervical cancer cell increased cervical cancer cell colonization (Kim et al., 2000). We therefore evaluated the impact of the Antp-AAC-11-LZ (363-399) peptide on migration of the highly invasive bone osteosarcoma U2OS cells using a using transwell Boyden chamber migration assay. As shown in FIG. 10A, Antp-AAC-11-LZ (377-399) peptide treatment substantially decreased U2OS cells migration, whereas the AAC-11-LZ (377-399) peptide didn't show any effect. Similar results were observed with the Antp-AAC-11-LZ (363-399) or the TAT-AAC-11-LZ (363-399) peptide. Of note, neither peptides impaired proliferation of the U2OS cells at the used concentrations, thus ruling out the possibility that impaired migration was a consequence of decreased proliferation. We next evaluated whether the Antp-AAC-11-LZ (377-399) peptide could hamper cell invasion. As shown in FIG. 10B, in an "invasion" assay, in which cells migrated though serial barriers consisting of a Matrigel layer and the porous filter, the Antp-AAC-11-LZ (377-399) peptide prevented invasion of the U2OS cells, whereas the AAC-11-LZ (377-399) peptide didn't show any effect.

Figure 11A:
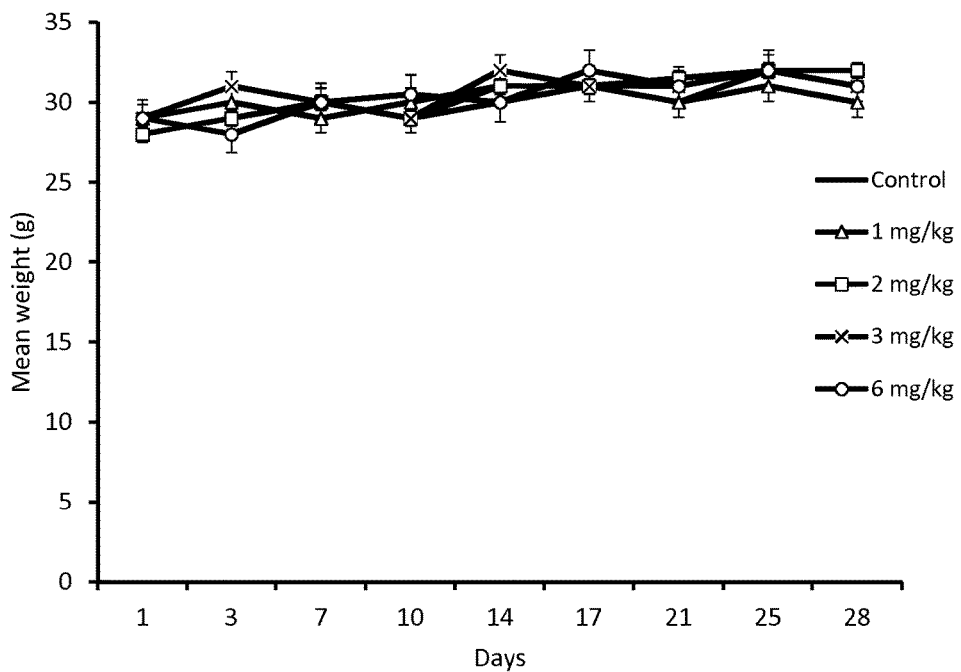

Systemic Delivery of the Antp-AAC-11-LZ (377-399) Peptide Inhibits Tumor Growth in A549 Non-Small Cell Lung Cancer Xenograft Mouse Models The inventors next investigated the effect of the AAC-11-LZ (377-399) peptide on distant solid tumor growth by using A549 non-small cell lung cancer xenograft mouse models. We first evaluated the toxicity of the Antp-AAC-11-LZ (377-399) peptide in nude mice that were injected intraperitoneally twice per week for 4 weeks with the Antp-AAC-11-LZ (377-399) peptide or normal saline solution (dose range: 1-6 mg peptide/kg body weight; n=3-4 mice per group). No mice died during the experiment and there was no significant difference between the different groups in body weight (FIG. 11A). At the end of the experiment, no obvious toxicity was observed to the kidney, lungs, heart, liver, pancreas and spleen of mice injected with the peptide.

Figure 11B:
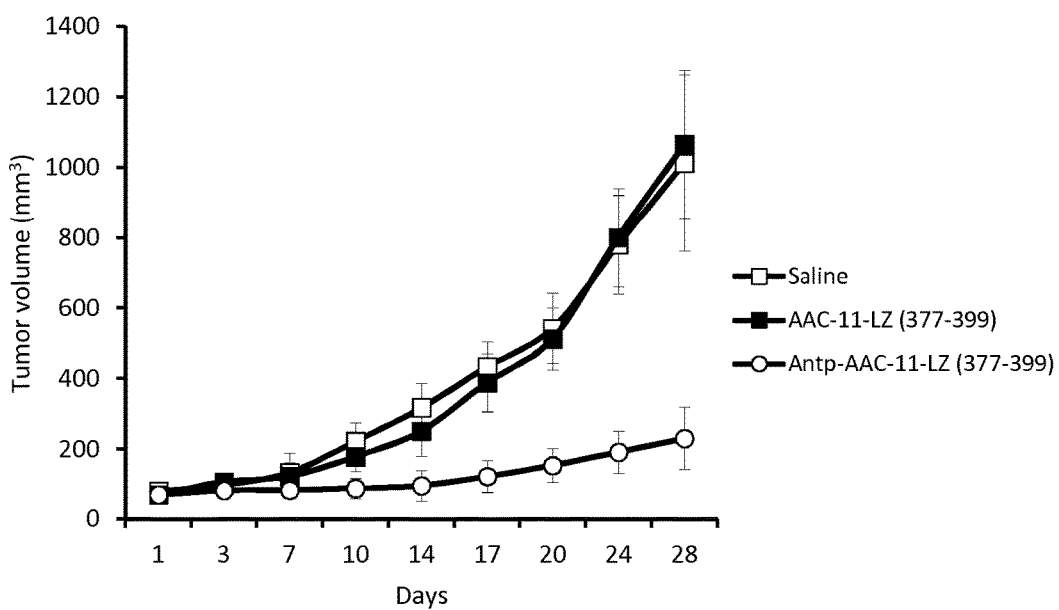

The inventors then evaluated the ability of the Antp-AAC-11-LZ (377-399) peptide to inhibit tumor growth using A549 non-small cell lung cancer xenograft models. As shown in FIG. 11B, mice treated with the Antp-AAC-11-LZ (377-399) peptide developed significantly smaller tumors than mice treated with AAC-11-LZ (377-399 peptide or vehicle. Indeed, tumors in mice receiving the AAC-11 LZ (377-399) peptide reached a final mean volume less than 25% of that of tumors in the control-treated mice (p=0.01). These data demonstrate that the Antp-AAC-11-LZ (377-399) peptide can inhibit by itself the growth of already formed and aggressively proliferating tumors.

TABLE 1 amino acid sequence of Penetratin-lined AAC-11 LZ-derived peptides

| Name | Sequence |
| --- | --- |
| Penetratin alone | RQIKIWFKKQNRRMKWKK (SEQ ID NO: 2) |
| AAC-11-LZ (363-399) | AKLNAEKLKDFKIRLQYFARGLQVYIRQLRLALQGKT (SEQ ID NO: 3) |
| Antp-AAC-11-LZ (363-399) | RQIKIWFKKQNRRMKWKKAKLNAEKLKDFKIRLQYFARGLQVYIRQLRLALQGKT (SEQ ID NO: 4) |
| Antp-AAC-11-LZ (363-399)L/G | RQIKIWFKKQNRRMKWKKAKLNAEKLKDFKIRGQYFARGGQVYIRQGRLALQGKT (SEQ ID NO: 5) |
| Antp-AAC-11-LZ (371-399) | RQIKIWFKKQNRRMKWKKKDFKIRLQYFARGLQVYIRQLRLALQGKT (SEQ ID NO: 6) |
| Antp-AAC-11-LZ (371-397) | RQIKIWFKKQNRRMKWKKKDFKIRLQYFARGLQVYIRQLRLALQG (SEQ ID NO: 7) |
| Antp-AAC-11-LZ (371-391) | RQIKIWFKKQNRRMKWKKKDFKIRLQYFARGLQVYIRQL (SEQ ID NO: 8) |
| Antp-AAC-11-LZ (377-399) | RQIKIWFKKQNRRMKWKKLQYFARGLQVYIRQLRLALQGKT (SEQ ID NO: 9) |
| Antp-AAC-11-LZ (380-399) | RQIKIWFKKQNRRMKWKKFARGLQVYIRQLRLALQGKT (SEQ ID NO: 10) |
| Cter-Antp-AAC-11-LZ (363-399) | AKLNAEKLKDFKIRLQYFARGLQVYIRQLRLALQGKTRQIKIWFKKQNRRMKWKK (SEQ ID NO: 11) |
| AAC-11-LZ (377-399) | LQYFARGLQVYIRQLRLALQGKT (SEQ ID NO: 16) |
| Antp-AAC-11-LZ (377-399 Δ385-390) | RQIKIWFKKQNRRMKWKKLQYFARGLLRLALQGKT (SEQ ID NO: 17) |

TABLE 2 amino acid sequence of TAT-lined AAC-11 LZ-derived peptides

| Name | Sequence |
| --- | --- |
| TAT alone | YGRKKRRQRRR (SEQ ID NO: 12) |
| AAC-11 LZ (363-399) | AKLNAEKLKDFKIRLQYFARGLQVYIRQLRLALQGKT (SEQ ID NO: 3) |
| TAT-AAC-11-LZ (363-399) | YGRKKRRQRRRGGGAKLNAEKLKDFKIRLQYFARGLQVYIRQLRLALQGKT (SEQ ID NO: 13) |
| TAT-AAC-11-LZ (363-399)RI (D-amino acids) | RRRQRRKKRGYGTKGQLALRLQRIYVQLGRAFYQLRIKFDKLKEANLKA (SEQ ID NO: 14) |

TABLE 3

Cell-penetrating peptides.

| Name | Sequence | Reference |
| --- | --- | --- |
| Penetratin | RQIKIWFKKQNRRMKWKK | U.S. Pat. No. 5,888,762 |
| TAT (47-57) | YGRKKRRQRRR | Wender, PA. et al., Proc. Natl. Acad. Sci. USA 97, 13003 (2000) |
| TAT (47-57) (RI) | RRRQRRKKRGY (D-amino acids) | SEQ ID NO: 15 |

REFERENCES

Throughout this application, various references describe the state of the art to which this invention pertains. The disclosures of these references are hereby incorporated by reference into the present disclosure.

Abuchowski, A., van Es, T., Palczuk, N. C., and Davis, F. F. (1977). Alteration of immunological properties of bovine serum albumin by covalent attachment of polyethylene glycol. The Journal of biological chemistry 252, 3578-3581.

Bechara, C., and Sagan, S. (2013). Cell-penetrating peptides: 20 years later, where do we stand? FEBS letters 587, 1693-1702.

Boohaker, R. J., Lee, M. W., Vishnubhotla, P., Perez, J. M., and Khaled, A. R. (2012). The use of therapeutic peptides to target and to kill cancer cells. Current medicinal chemistry 19, 3794-3804.

Brady, G., Jantzen, H. M., Bernard, H. U., Brown, R., Schutz, G., and Hashimoto-Gotoh, T. (1984). New cosmid vectors developed for eukaryotic DNA cloning. Gene 27, 223-232.

Brown, D., Kogan, S., Lagasse, E., Weissman, I., Alcalay, M., Pelicci, P. G., Atwater, S., and Bishop, J. M. (1997). A PMLRARalpha transgene initiates murine acute promyelocytic leukemia. Proceedings of the National Academy of Sciences of the United States of America 94, 2551-2556.

Chapman, A. P. (2002). PEGylated antibodies and antibody fragments for improved therapy: a review. Advanced drug delivery reviews 54, 531-545.

Choi, Y. S., Lee, J. Y., Suh, J. S., Lee, S. J., Yang, V. C., Chung, C. P., and Park, Y. J. (2011). Cell penetrating peptides for tumor targeting. Current pharmaceutical biotechnology 12, 1166-1182.

Chorev, M., and Goodman, M. (1995). Recent developments in retro peptides and proteins—an ongoing topochemical exploration. Trends in biotechnology 13, 438-445.

Clegg, N., Ferguson, C., True, L. D., Arnold, H., Moorman, A., Quinn, J. E., Vessella, R. L., and Nelson, P. S. (2003). Molecular characterization of prostatic small-cell neuroendocrine carcinoma. The Prostate 55, 55-64.

Fischer, P. M. (2003). The design, synthesis and application of stereochemical and directional peptide isomers: a critical review. Current protein & peptide science 4, 339-356.

Gillies, S. D., Morrison, S. L., Oi, V. T., and Tonegawa, S. (1983). A tissue-specific transcription enhancer element is located in the major intron of a rearranged immunoglobulin heavy chain gene. Cell 33, 717-728.

Heitz, F., Morris, M. C., and Divita, G. (2009). Twenty years of cell-penetrating peptides: from molecular mechanisms to therapeutics. British journal of pharmacology 157, 195-206.

Janin, Y. L. (2003). Peptides with anticancer use or potential. Amino acids 25, 1-40.

Jones, A. T., and Sayers, E. J. (2012). Cell entry of cell penetrating peptides: tales of tails wagging dogs. Journal of controlled release: official journal of the Controlled Release Society 161, 582-591.

Karlin, S., and Altschul, S. F. (1990). Methods for assessing the statistical significance of molecular sequence features by using general scoring schemes. Proceedings of the National Academy of Sciences of the United States of America 87, 2264-2268.

Khafagy el, S., and Morishita, M. (2012). Oral biodrug delivery using cell-penetrating peptide. Advanced drug delivery reviews 64, 531-539.

Kim, J. W., Cho, H. S., Kim, J. H., Hur, S. Y., Kim, T. E., Lee, J. M., Kim, I. K., and Namkoong, S. E. (2000). AAC-11 overexpression induces invasion and protects cervical cancer cells from apoptosis. Laboratory investigation; a journal of technical methods and pathology 80, 587-594.

Kjonniksen, I., Storeng, R., Pihl, A., McLemore, T. L., and Fodstad, O. (1989). A human tumor lung metastasis model in athymic nude rats. Cancer research 49, 5148-5152.

Kogan, S. C., Hong, S. H., Shultz, D. B., Privalsky, M. L., and Bishop, J. M. (2000). Leukemia initiated by PMLR-ARalpha: the PML domain plays a critical role while retinoic acid-mediated transactivation is dispensable. Blood 95, 1541-1550.

Krejci, P., Pejchalova, K., Rosenbloom, B. E., Rosenfelt, F. P., Tran, E. L., Laurell, H., and Wilcox, W. R. (2007). The antiapoptotic protein Api5 and its partner, high molecular weight FGF2, are up-regulated in B cell chronic lymphoid leukemia. Journal of leukocyte biology 82, 1363-1364.

Kuwana, Y., Asakura, Y., Utsunomiya, N., Nakanishi, M., Arata, Y., Itoh, S., Nagase, F., and Kurosawa, Y. (1987). Expression of chimeric receptor composed of immunoglobulin-derived V regions and T-cell receptor-derived C regions. Biochemical and biophysical research communications 149, 960-968.

Lallemand-Breitenbach, V., Guillemin, M. C., Janin, A., Daniel, M. T., Degos, L., Kogan, S. C., Bishop, J. M., and de The, H. (1999). Retinoic acid and arsenic synergize to eradicate leukemic cells in a mouse model of acute promyelocytic leukemia. The Journal of experimental medicine 189, 1043-1052.

Li, G. N., Wang, S. P., Xue, X., Qu, X. J., and Liu, H. P. (2013). Monoclonal antibody-related drugs for cancer therapy. Drug discoveries & therapeutics 7, 178-184.

Malhi, S. S., and Murthy, R. S. (2012). Delivery to mitochondria: a narrower approach for broader therapeutics. Expert opinion on drug delivery 9, 909-935.

Marangoni, E., Vincent-Salomon, A., Auger, N., Degeorges, A., Assayag, F., de Cremoux, P., de Plater, L., Guyader, C., De Pinieux, G., Judde, J. G., et al. (2007). A new model of patient tumor-derived breast cancer xenografts for preclinical assays. Clin Cancer Res 13, 3989-3998.

Mason, J. O., Williams, G. T., and Neuberger, M. S. (1985). Transcription cell type specificity is conferred by an immunoglobulin VH gene promoter that includes a functional consensus sequence. Cell 41, 479-487.

Miyaji, H., Harada, N., Mizukami, T., Sato, S., Fujiyoshi, N., and Itoh, S. (1990). Expression of human lymphotoxin in Namalwa KJM-1 cells adapted to serum-free medium. Cytotechnology 4, 39-43.

Mizukami, T., and Itoh, S. (1987). A new SV40-based vector developed for cDNA expression in animal cells. Journal of biochemistry 101, 1307-1310.

Monfardini, C., Kieber-Emmons, T., VonFeldt, J. M., O'Malley, B., Rosenbaum, H., Godillot, A. P., Kaushansky, K., Brown, C. B., Voet, D., McCallus, D. E., et al. (1995). Recombinant antibodies in bioactive peptide design. The Journal of biological chemistry 270, 6628-6638.

Morris, E. J., Michaud, W. A., Ji, J. Y., Moon, N. S., Rocco, J. W., and Dyson, N. J. (2006). Functional identification of Api5 as a suppressor of E2F-dependent apoptosis in vivo. PLoS genetics 2, e196.

O'Hare, K., Benoist, C., and Breathnach, R. (1981). Transformation of mouse fibroblasts to methotrexate resistance by a recombinant plasmid expressing a prokaryotic dihydrofolate reductase. Proceedings of the National Academy of Sciences of the United States of America 78, 1527-1531.

Rigou, P., Piddubnyak, V., Faye, A., Rain, J. C., Michel, L., Calvo, F., and Poyet, J. L. (2009). The antiapoptotic protein AAC-11 interacts with and regulates Acinus-mediated DNA fragmentation. The EMBO journal 28, 1576-1588.

Sasaki, H., Moriyama, S., Yukiue, H., Kobayashi, Y., Nakashima, Y., Kaji, M., Fukai, I., Kiriyama, M., Yamakawa, Y., and Fujii, Y. (2001). Expression of the antiapoptosis gene, AAC-11, as a prognosis marker in non-small cell lung cancer. Lung cancer (Amsterdam, Netherlands) 34, 53-57.

Sliwkowski, M. X., and Mellman, I. (2013). Antibody therapeutics in cancer. Science (New York, N.Y. 341, 1192-1198.

Tewari, M., Yu, M., Ross, B., Dean, C., Giordano, A., and Rubin, R. (1997). AAC-11, a novel cDNA that inhibits apoptosis after growth factor withdrawal. Cancer research 57, 4063-4069.

Van den Berghe, L., Laurell, H., Huez, I., Zanibellato, C., Prats, H., and Bugler, B. (2000). FIF [fibroblast growth factor-2 (FGF-2)-interacting-factor], a nuclear putatively antiapoptotic factor, interacts specifically with FGF-2. Molecular endocrinology (Baltimore, Md. 14, 1709-1724.

Varna, M., Lehmann-Che, J., Turpin, E., Marangoni, E., El-Bouchtaoui, M., Jeanne, M., Grigoriu, C., Ratajczak, P., Leboeuf, C., Plassa, L. F., et al. (2009). p53 dependent cell-cycle arrest triggered by chemotherapy in xenografted breast tumors. International journal of cancer Journal international du cancer 124, 991-997.

The invention claimed is:

1. A polypeptide which consists of:
   i) an amino acid sequence ranging from a phenylalanine residue at position 380 to a leucine residue at position 384 in SEQ ID NO: 1, or
   ii) an amino acid sequence which is a retro-inverso of the amino acid sequence ranging from the phenylalanine residue at position 380 to the leucine residue at position 384 in SEQ ID NO: 1.

2. A polypeptide which consists of:
   i) an amino acid sequence ranging from the phenylalanine residue at position 380 to an isoleucine residue at position 388 in SEQ ID NO:1, or
   ii) an amino acid sequence having at least 70% identity with the amino acid sequence ranging from the phenylalanine residue at position 380 to the isoleucine residue at position 388 in SEQ ID NO:1, or
   iii) an amino acid sequence which is a retro-inverso of the amino acid sequence ranging from the phenylalanine residue at position 380 to the isoleucine residue at position 388 in SEQ ID NO:1, or
   iv) an amino acid sequence which is retro-inverso of the amino acid sequence having at least 70% of identity with the amino acid sequence ranging from the phenylalanine residue at position 380 to the isoleucine residue at position 388 in SEQ ID NO:1.

3. A polypeptide which consists of:
   i) an amino acid sequence ranging from the phenylalanine residue at position 380 to a leucine residue at position 391 in SEQ ID NO:1, or
   ii) an amino acid sequence having at least 70% of identity with the amino acid sequence ranging from the phenylalanine residue at position 380 to the leucine residue at position 391 in SEQ ID NO:1, or
   iii) an amino acid sequence which is a retro-inverso of the amino acid sequence ranging from the phenylalanine residue at position 380 to the leucine residue at position 391 in SEQ ID NO:1, or
   iv) an amino acid sequence which is retro-inverso of the amino acid sequence having at least 70% of identity with the amino acid sequence ranging from the phenylalanine residue at position 380 to the leucine residue at position 391 in SEQ NO:1.

4. A polypeptide which consists of:
   i) an amino acid sequence ranging from a tyrosine residue at position 379 to a leucine residue at position 391 in SEQ ID NO:1, or
   ii) an amino acid sequence having at least 70% of identity with the amino acid sequence ranging from the tyrosine residue at position 379 to the leucine residue at position 391 in SEQ ID NO:1, or
   iii) an amino acid sequence which is a retro-inverso of the amino acid sequence ranging from the tyrosine residue at position 379 to the leucine residue at position 391 in SEQ ID NO:1, or
   iv) an amino acid sequence which is retro-inverso having at least 70% of identity with the amino acid sequence ranging from the tyrosine residue at position 379 to the leucine residue at position 391 in SEQ ID NO:1.

5. A polypeptide which consists of:
i) an amino acid sequence ranging from a glutamine residue at position 378 to a leucine residue at position 391 in SEQ ID NO:1, or
ii) an amino acid sequence having at least 70% of identity with the amino acid sequence ranging from glutamine residue at position 378 to the leucine residue at position 391 in SEQ ID NO:1, or
iii) an amino acid sequence which is a retro-inverso of the amino acid sequence ranging from glutamine residue at position 378 to the leucine residue at position 391 in SEQ ID NO:1, or
iv) an amino acid sequence which is retro-inverso having at least 70% of identity with the amino acid sequence ranging from glutamine residue at position 378 to the leucine residue at position 391 in SEQ ID NO:1.

6. A polypeptide which consists of:
i) an amino acid sequence ranging from a leucine residue at position 377 to a leucine residue at position 391 in SEQ ID NO:1, or
ii) an amino acid sequence having at least 70% of identity with the amino acid sequence ranging from the leucine residue at position 377 to the leucine residue at position 391 in SEQ ID NO:1, or
iii) an amino acid sequence which is a retro-inverso of the amino acid sequence ranging from the leucine residue at position 377 to the leucine residue at position 391 in SEQ ID NO:1, or
iv) an amino acid sequence which is retro-inverso having at least 70% of identity with the amino acid sequence ranging from the leucine residue at position 377 to the leucine residue at position 391 in SEQ ID NO:1.

7. A polypeptide which consists of:
i) an amino acid sequence ranging from a lysine residue at position 371 to a glycine residue at position 397 in SEQ ID NO:1, or
ii) an amino acid sequence having at least 70% of identity with the amino acid sequence ranging from the lysine residue at position 371 to the glycine residue at position 397 in SEQ ID NO:1, or
iii) an amino acid sequence which is a retro-inverso of the amino acid sequence ranging from the lysine residue at position 371 to the glycine residue at position 397 in SEQ ID NO:1, or
iv) an amino acid sequence which is retro-inverso having at least 70% of identity with the amino acid sequence ranging from the lysine residue at position 371 to the glycine residue at position 397 in SEQ ID NO:1.

8. A polypeptide which consists of:
i) an amino acid sequence ranging from a lysine residue at position 371 to a leucine residue at position 391 in SEQ ID NO:1, or
ii) an amino acid sequence having at least 70% of identity with the amino acid sequence ranging from the lysine residue at position 371 to the leucine residue at position 391 in SEQ ID NO:1, or
iii) an amino acid sequence which is a retro-inverso of the amino acid sequence ranging from the lysine residue at position 371 to the leucine residue at position 391 in SEQ ID NO:1, or
iv) an amino acid sequence which is retro-inverso having at least 70% of identity with the amino acid sequence ranging from the lysine residue at position 371 to the leucine residue at position 391 in SEQ ID NO:1.

9. A polypeptide which consists of:
i) an amino acid sequence ranging from the phenylalanine residue at position 380 to a threonine residue at position 399 in SEQ ID NO:1, or
ii) an amino acid sequence having at least 70% of identity with the amino acid sequence ranging from the phenylalanine residue at position 380 to the threonine residue at position 399 in SEQ ID NO:1, or
iii) an amino acid sequence which is a retro-inverso of the amino acid sequence ranging from the phenylalanine residue at position 380 to the threonine residue at position 399 in SEQ ID NO:1, or
iv) an amino acid sequence which is retro-inverso having at least 70% of identity with the amino acid sequence ranging from the phenylalanine residue at position 380 to the threonine residue at position 399 in SEQ ID NO:1.

10. A polypeptide which consists of:
i) an amino acid sequence ranging from a lysine residue at position 371 to a threonine residue at position 399 in SEQ ID NO:1, or
ii) an amino acid sequence having at least 70% of identity with the amino acid sequence ranging from the lysine residue at position 371 to the threonine residue at position 399 in SEQ ID NO:1, or
iii) an amino acid sequence which is a retro-inverso of the amino acid sequence ranging from the lysine residue at position 371 to the threonine residue at position 399 in SEQ ID NO:1, or
iv) an amino acid sequence which is retro-inverso having at least 70% of identity with the amino acid sequence ranging from the lysine residue at position 371 to the threonine residue at position 399 in SEQ ID NO:1.

11. A polypeptide which consists of:
i) an amino acid sequence ranging from a leucine residue at position 377 to a threonine residue at position 399 in SEQ ID NO:1, or
ii) an amino acid sequence having at least 70% of identity with the amino acid sequence ranging from the leucine residue at position 377 to the threonine residue at position 399 in SEQ ID NO:1, or
iii) an amino acid sequence which is a retro-inverso of the amino acid sequence ranging from the leucine residue at position 377 to the threonine residue at position 399 in SEQ ID NO:1, or
iv) an amino acid sequence which is retro-inverso having at least 70% of identity with the amino acid sequence ranging from the leucine residue at position 377 to the threonine residue at position 399 in SEQ ID NO:1.

12. A fusion protein comprising
I. a polypeptide which consists of:
i) an amino acid sequence ranging from a phenylalanine residue at position 380 to a leucine residue at position 388 in SEQ ID NO:1, or
ii) an amino acid sequence having at least 70% of identity with the amino acid sequence ranging from the phenylalanine residue at position 380 to the leucine residue at position 388 in SEQ ED NO:1, or
iii) an amino acid sequence which is a retro-inverso of the amino acid sequence ranging from the phenylalanine residue at position 380 to the leucine residue at position 388 in SEQ ID NO:1, or
iv) an amino acid sequence which is retro-inverso of the amino acid sequence having at least 70% of identity with the amino acid sequence ranging from the phenylalanine residue at position 380 to the leucine residue at position 388 in SEQ ID NO:1, and
II. at least one heterologous polypeptide.

13. The fusion protein of claim 12 wherein the last amino acid of the C-terminal end of said polypeptide is directly linked by a covalent bond to the first amino acid of the N-terminal end of said at least one heterologous polypeptide, or the first amino acid of the N-terminal end of said polypeptide is directly linked by a covalent bond to the last amino acid of the C-terminal end of said at least one heterologous polypeptide.

14. The fusion protein of claim 12 wherein the heterologous polypeptide is a cell-penetrating peptide.

15. The fusion protein of claim 12 wherein the heterologous polypeptide is an internalization sequence derived either from the homeodomain of Drosophila Antennapedia/Penetratin (Antp) protein or the Transactivator of Transcription (TAT) cell penetrating sequence (SEQ ID NO: 12).

16. The fusion protein of claim 12 which comprises or consists of a sequence selected from the group consisting of SEQ ID NO:6; SEQ ID NO:7, SEQ ID NO:8, SEQ ID NO:9, SEQ ID NO:10; SEQ ID NO:16; and SEQ ID NO:17.

17. A method for treating a cancer in a subject in need thereof comprising administering to the subject a therapeutically effective amount of a) a polypeptide which consists of:
  i) an amino acid sequence ranging from a phenylalanine residue at position 380 to a leucine residue at position 384 in SEQ ID NO:1, or
  ii) an amino acid sequence having at least 70% of identity with the amino acid sequence ranging from the phenylalanine residue at position 380 to the leucine residue at position 384 in SEQ ID NO:1, or
  iii) an amino acid sequence which is a retro-inverso of the amino acid sequence ranging from the phenylalanine residue at position 380 to the leucine residue at position 384 in SEQ ID NO:1, or
  iv) an amino acid sequence which is retro-inverso of the amino acid sequence having at least 70% of identity with the amino acid sequence ranging from the phenylalanine residue at position 380 to the leucine residue at position 384 in SEQ ID NO:1, or
  b) a fusion protein comprising the polypeptide.

18. The method of claim 17 wherein the cancer is selected from the group consisting of breast cancer, triple-negative breast cancer, Acute Promyelocytic Leukemia (AML), hematologic cancer, lymphoma, B cell lymphoma, T cell lymphoma, B-cell non-Hodgkin's lymphoma, T-acute lymphoblastic leukemia, lung adenocarcinoma, kidney cancer, ovarian carcinoma, colon carcinoma, melanoma, and Sezary syndrome.

19. A pharmaceutical composition comprising
a polypeptide which consists of:
  i) an amino acid sequence ranging from a phenylalanine residue at position 380 to a leucine residue at position 388 in SEQ ID NO:1, or
  ii) an amino acid sequence having at least 70% of identity with the amino acid sequence ranging from the phenylalanine residue at position 380 to the leucine residue at position 388 in SEQ ID NO:1, or
  iii) an amino acid sequence which is a retro-inverso of the amino acid sequence ranging from the phenylalanine residue at position 380 to the leucine residue at position 388 in SEQ ID NO:1, or
  iv) an amino acid sequence which is retro-inverso of the amino acid sequence having at least 70% of identity with the amino acid sequence ranging from the phenylalanine residue at position 380 to the leucine residue at position 388 in SEQ ID NO:1, or
a fusion protein comprising the polypeptide.

* * * * *

SEQUENCE LISTING

```
<160> NUMBER OF SEQ ID NOS: 17

<210> SEQ ID NO 1
<211> LENGTH: 524
<212> TYPE: PRT
<213> ORGANISM: Homo sapiens

<400> SEQUENCE: 1

Met Pro Thr Val Glu Glu Leu Tyr Arg Asn Tyr Gly Ile Leu Ala Asp
1               5                   10                  15

Ala Thr Glu Gln Val Gly Gln His Lys Asp Ala Tyr Gln Val Ile Leu
            20                  25                  30

Asp Gly Val Lys Gly Gly Thr Lys Glu Lys Arg Leu Ala Ala Gln Phe
        35                  40                  45

Ile Pro Lys Phe Phe Lys His Phe Pro Glu Leu Ala Asp Ser Ala Ile
    50                  55                  60

Asn Ala Gln Leu Asp Leu Cys Glu Asp Glu Asp Val Ser Ile Arg Arg
65                  70                  75                  80

Gln Ala Ile Lys Glu Leu Pro Gln Phe Ala Thr Gly Glu Asn Leu Pro
                85                  90                  95

Arg Val Ala Asp Ile Leu Thr Gln Leu Leu Gln Thr Asp Asp Ser Ala
            100                 105                 110

Glu Phe Asn Leu Val Asn Asn Ala Leu Leu Ser Ile Phe Lys Met Asp
        115                 120                 125

Ala Lys Gly Thr Leu Gly Gly Leu Phe Ser Gln Ile Leu Gln Gly Glu
    130                 135                 140

Asp Ile Val Arg Glu Arg Ala Ile Lys Phe Leu Ser Thr Lys Leu Lys
145                 150                 155                 160

Thr Leu Pro Asp Glu Val Leu Thr Lys Glu Val Glu Glu Leu Ile Leu
                165                 170                 175

Thr Glu Ser Lys Lys Val Leu Glu Asp Val Thr Gly Glu Glu Phe Val
            180                 185                 190

Leu Phe Met Lys Ile Leu Ser Gly Leu Lys Ser Leu Gln Thr Val Ser
        195                 200                 205

Gly Arg Gln Gln Leu Val Glu Leu Val Ala Glu Gln Ala Asp Leu Glu
    210                 215                 220

Gln Thr Phe Asn Pro Ser Asp Pro Asp Cys Val Asp Arg Leu Leu Gln
225                 230                 235                 240

Cys Thr Arg Gln Ala Val Pro Leu Phe Ser Lys Asn Val His Ser Thr
                245                 250                 255

Arg Phe Val Thr Tyr Phe Cys Glu Gln Val Leu Pro Asn Leu Gly Thr
            260                 265                 270
```

-continued

```
Leu Thr Thr Pro Val Glu Gly Leu Asp Ile Gln Leu Glu Val Leu Lys
            275                 280                 285

Leu Leu Ala Glu Met Ser Ser Phe Cys Gly Asp Met Glu Lys Leu Glu
        290                 295                 300

Thr Asn Leu Arg Lys Leu Phe Asp Lys Leu Leu Glu Tyr Met Pro Leu
305                 310                 315                 320

Pro Pro Glu Glu Ala Glu Asn Gly Glu Asn Ala Gly Asn Glu Glu Pro
                325                 330                 335

Lys Leu Gln Phe Ser Tyr Val Glu Cys Leu Leu Tyr Ser Phe His Gln
            340                 345                 350

Leu Gly Arg Lys Leu Pro Asp Phe Leu Thr Ala Lys Leu Asn Ala Glu
        355                 360                 365

Lys Leu Lys Asp Phe Lys Ile Arg Leu Gln Tyr Phe Ala Arg Gly Leu
    370                 375                 380

Gln Val Tyr Ile Arg Gln Leu Arg Leu Ala Leu Gln Gly Lys Thr Gly
385                 390                 395                 400

Glu Ala Leu Lys Thr Glu Glu Asn Lys Ile Lys Val Val Ala Leu Lys
                405                 410                 415

Ile Thr Asn Asn Ile Asn Val Leu Ile Lys Asp Leu Phe His Ile Pro
            420                 425                 430

Pro Ser Tyr Lys Ser Thr Val Thr Leu Ser Trp Lys Pro Val Gln Lys
        435                 440                 445

Val Glu Ile Gly Gln Lys Arg Ala Ser Glu Asp Thr Thr Ser Gly Ser
    450                 455                 460

Pro Pro Lys Lys Ser Ser Ala Gly Pro Lys Arg Asp Ala Arg Gln Ile
465                 470                 475                 480

Tyr Asn Pro Pro Ser Gly Lys Tyr Ser Ser Asn Leu Gly Asn Phe Asn
                485                 490                 495

Tyr Glu Gln Arg Gly Ala Phe Arg Gly Ser Arg Gly Gly Arg Gly Trp
            500                 505                 510

Gly Thr Arg Gly Asn Arg Ser Arg Gly Arg Leu Tyr
        515                 520

<210> SEQ ID NO 2
<211> LENGTH: 18
<212> TYPE: PRT
<213> ORGANISM: Artificial
<220> FEATURE:
<223> OTHER INFORMATION: Synthetic Penetratin

<400> SEQUENCE: 2

Arg Gln Ile Lys Ile Trp Phe Lys Lys Gln Asn Arg Arg Met Lys Trp
1               5                   10                  15

Lys Lys

<210> SEQ ID NO 3
<211> LENGTH: 37
<212> TYPE: PRT
<213> ORGANISM: Artificial
<220> FEATURE:
<223> OTHER INFORMATION: Synthetic AAC-11-LZ (363-399)
```

```
<400> SEQUENCE: 3

Ala Lys Leu Asn Ala Glu Lys Leu Lys Asp Phe Lys Ile Arg Leu Gln
1               5                   10                  15

Tyr Phe Ala Arg Gly Leu Gln Val Tyr Ile Arg Gln Leu Arg Leu Ala
            20                  25                  30

Leu Gln Gly Lys Thr
            35

<210> SEQ ID NO 4
<211> LENGTH: 55
<212> TYPE: PRT
<213> ORGANISM: Artificial
<220> FEATURE:
<223> OTHER INFORMATION: Synthetic Antp-AAC-11-LZ (363-399)

<400> SEQUENCE: 4

Arg Gln Ile Lys Ile Trp Phe Lys Lys Gln Asn Arg Arg Met Lys Trp
1               5                   10                  15

Lys Lys Ala Lys Leu Asn Ala Glu Lys Leu Lys Asp Phe Lys Ile Arg
            20                  25                  30

Leu Gln Tyr Phe Ala Arg Gly Leu Gln Val Tyr Ile Arg Gln Leu Arg
        35                  40                  45

Leu Ala Leu Gln Gly Lys Thr
    50                  55

<210> SEQ ID NO 5
<211> LENGTH: 55
<212> TYPE: PRT
<213> ORGANISM: Artificial
<220> FEATURE:
<223> OTHER INFORMATION: Synthetic Antp-AAC-11-LZ (363-399)L/G

<400> SEQUENCE: 5

Arg Gln Ile Lys Ile Trp Phe Lys Lys Gln Asn Arg Arg Met Lys Trp
1               5                   10                  15

Lys Lys Ala Lys Leu Asn Ala Glu Lys Leu Lys Asp Phe Lys Ile Arg
            20                  25                  30

Gly Gln Tyr Phe Ala Arg Gly Gly Gln Val Tyr Ile Arg Gln Gly Arg
        35                  40                  45

Leu Ala Leu Gln Gly Lys Thr
    50                  55

<210> SEQ ID NO 6
<211> LENGTH: 47
<212> TYPE: PRT
<213> ORGANISM: Artificial
<220> FEATURE:
<223> OTHER INFORMATION: Synthetic Antp-AAC-11-LZ (371-399)

<400> SEQUENCE: 6

Arg Gln Ile Lys Ile Trp Phe Lys Lys Gln Asn Arg Arg Met Lys Trp
1               5                   10                  15

Lys Lys Lys Asp Phe Lys Ile Arg Leu Gln Tyr Phe Ala Arg Gly Leu
            20                  25                  30

Gln Val Tyr Ile Arg Gln Leu Arg Leu Ala Leu Gln Gly Lys Thr
        35                  40                  45

<210> SEQ ID NO 7
<211> LENGTH: 45
<212> TYPE: PRT
<213> ORGANISM: Artificial
```

```
<220> FEATURE:
<223> OTHER INFORMATION: Synthetic Antp-AAC-11-LZ (371-397)

<400> SEQUENCE: 7

Arg Gln Ile Lys Ile Trp Phe Lys Lys Gln Asn Arg Arg Met Lys Trp
1               5                   10                  15

Lys Lys Lys Asp Phe Lys Ile Arg Leu Gln Tyr Phe Ala Arg Gly Leu
            20                  25                  30

Gln Val Tyr Ile Arg Gln Leu Arg Leu Ala Leu Gln Gly
        35                  40                  45

<210> SEQ ID NO 8
<211> LENGTH: 39
<212> TYPE: PRT
<213> ORGANISM: Artificial
<220> FEATURE:
<223> OTHER INFORMATION: Synthetic Antp-AAC-11-LZ (371-391)

<400> SEQUENCE: 8

Arg Gln Ile Lys Ile Trp Phe Lys Lys Gln Asn Arg Arg Met Lys Trp
1               5                   10                  15

Lys Lys Lys Asp Phe Lys Ile Arg Leu Gln Tyr Phe Ala Arg Gly Leu
            20                  25                  30

Gln Val Tyr Ile Arg Gln Leu
        35

<210> SEQ ID NO 9
<211> LENGTH: 41
<212> TYPE: PRT
<213> ORGANISM: Artificial
<220> FEATURE:
<223> OTHER INFORMATION: Synthetic Antp-AAC-11-LZ (377-399)

<400> SEQUENCE: 9

Arg Gln Ile Lys Ile Trp Phe Lys Lys Gln Asn Arg Arg Met Lys Trp
1               5                   10                  15

Lys Lys Leu Gln Tyr Phe Ala Arg Gly Leu Gln Val Tyr Ile Arg Gln
            20                  25                  30

Leu Arg Leu Ala Leu Gln Gly Lys Thr
        35                  40

<210> SEQ ID NO 10
<211> LENGTH: 38
<212> TYPE: PRT
<213> ORGANISM: Artificial
<220> FEATURE:
<223> OTHER INFORMATION: Synthetic Antp-AAC-11-LZ (380-399)

<400> SEQUENCE: 10

Arg Gln Ile Lys Ile Trp Phe Lys Lys Gln Asn Arg Arg Met Lys Trp
1               5                   10                  15

Lys Lys Phe Ala Arg Gly Leu Gln Val Tyr Ile Arg Gln Leu Arg Leu
            20                  25                  30

Ala Leu Gln Gly Lys Thr
        35

<210> SEQ ID NO 11
<211> LENGTH: 55
<212> TYPE: PRT
<213> ORGANISM: Artificial
<220> FEATURE:
<223> OTHER INFORMATION: Synthetic Cter-Antp-AAC-11-LZ (363-399)
```

```
<400> SEQUENCE: 11

Ala Lys Leu Asn Ala Glu Lys Leu Lys Asp Phe Lys Ile Arg Leu Gln
1               5                   10                  15

Tyr Phe Ala Arg Gly Leu Gln Val Tyr Ile Arg Gln Leu Arg Leu Ala
            20                  25                  30

Leu Gln Gly Lys Thr Arg Gln Ile Lys Ile Trp Phe Lys Gln Asn
        35                  40                  45

Arg Arg Met Lys Trp Lys Lys
    50                  55

<210> SEQ ID NO 12
<211> LENGTH: 11
<212> TYPE: PRT
<213> ORGANISM: Artificial
<220> FEATURE:
<223> OTHER INFORMATION: Synthetic TAT alone

<400> SEQUENCE: 12

Tyr Gly Arg Lys Lys Arg Arg Gln Arg Arg Arg
1               5                   10

<210> SEQ ID NO 13
<211> LENGTH: 51
<212> TYPE: PRT
<213> ORGANISM: Artificial
<220> FEATURE:
<223> OTHER INFORMATION: Synthetic TAT-AAC-11-LZ (363-399)

<400> SEQUENCE: 13

Tyr Gly Arg Lys Lys Arg Arg Gln Arg Arg Arg Gly Gly Gly Ala Lys
1               5                   10                  15

Leu Asn Ala Glu Lys Leu Lys Asp Phe Lys Ile Arg Leu Gln Tyr Phe
            20                  25                  30

Ala Arg Gly Leu Gln Val Tyr Ile Arg Gln Leu Arg Leu Ala Leu Gln
        35                  40                  45

Gly Lys Thr
    50

<210> SEQ ID NO 14
<211> LENGTH: 49
<212> TYPE: PRT
<213> ORGANISM: Artificial
<220> FEATURE:
<223> OTHER INFORMATION: Synthetic TAT-AAC-11-LZ (363-399)RI  (D-amino
      acids)

<400> SEQUENCE: 14

Arg Arg Arg Gln Arg Arg Lys Lys Arg Gly Tyr Gly Thr Lys Gly Gln
1               5                   10                  15

Leu Ala Leu Arg Leu Gln Arg Ile Tyr Val Gln Leu Gly Arg Ala Phe
            20                  25                  30

Tyr Gln Leu Arg Ile Lys Phe Asp Lys Leu Lys Glu Ala Asn Leu Lys
        35                  40                  45

Ala

<210> SEQ ID NO 15
<211> LENGTH: 11
<212> TYPE: PRT
<213> ORGANISM: Artificial
<220> FEATURE:
<223> OTHER INFORMATION: Synthetic TAT (47-57) (RI)
```

```
<400> SEQUENCE: 15

Arg Arg Arg Gln Arg Arg Lys Lys Arg Gly Tyr
1               5                   10

<210> SEQ ID NO 16
<211> LENGTH: 23
<212> TYPE: PRT
<213> ORGANISM: Artificial
<220> FEATURE:
<223> OTHER INFORMATION: Synthetic AAC-11-LZ (377-399)

<400> SEQUENCE: 16

Leu Gln Tyr Phe Ala Arg Gly Leu Gln Val Tyr Ile Arg Gln Leu Arg
1               5                   10                  15

Leu Ala Leu Gln Gly Lys Thr
            20

<210> SEQ ID NO 17
<211> LENGTH: 35
<212> TYPE: PRT
<213> ORGANISM: Artificial
<220> FEATURE:
<223> OTHER INFORMATION: Synthetic Antp-AAC-11-LZ (377-399 ?385-390)

<400> SEQUENCE: 17

Arg Gln Ile Lys Ile Trp Phe Lys Lys Gln Asn Arg Arg Met Lys Trp
1               5                   10                  15

Lys Lys Leu Gln Tyr Phe Ala Arg Gly Leu Leu Arg Leu Ala Leu Gln
            20                  25                  30

Gly Lys Thr
        35
```